US008734391B2

(12) United States Patent
Yodfat et al.

(10) Patent No.: US 8,734,391 B2
(45) Date of Patent: May 27, 2014

(54) SYSTEMS, METHODS AND DEVICES FOR ADJUSTING THE INSERTION DEPTH OF A CANNULA ASSOCIATED WITH A PORTABLE THERAPEUTIC DEVICE

(75) Inventors: Ofer Yodfat, Modi'in (IL); Illai J. Gescheit, Tel Aviv (IL); Danna Perlman, Haifa (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 32 days.

(21) Appl. No.: 13/503,176

(22) PCT Filed: Oct. 28, 2010

(86) PCT No.: PCT/IL2010/000887
§ 371 (c)(1), (2), (4) Date: Jun. 29, 2012

(87) PCT Pub. No.: WO2011/051940
PCT Pub. Date: May 5, 2011

(65) Prior Publication Data

US 2012/0259185 A1 Oct. 11, 2012

Related U.S. Application Data

(60) Provisional application No. 61/256,326, filed on Oct. 30, 2009.

(51) Int. Cl.
*A61M 5/00* (2006.01)

(52) U.S. Cl.
USPC .......................................................... 604/117

(58) Field of Classification Search
USPC ............... 604/117, 264, 171, 164.01–167.06, 604/272, 523; 606/309
See application file for complete search history.

(56) References Cited

U.S. PATENT DOCUMENTS

2005/0137525 A1* 6/2005 Wang et al. ................ 604/93.01
2006/0200185 A1* 9/2006 Marchek et al. .............. 606/191
2006/0276747 A1 12/2006 Moos et al.
2008/0132838 A1* 6/2008 Wyrick ......................... 604/117
2008/0280505 A1* 11/2008 Ma et al. ....................... 439/801
2008/0319414 A1 12/2008 Yodfat et al.

FOREIGN PATENT DOCUMENTS

| | | | |
|---|---|---|---|
| DE | 29605069 | U1 | 6/1996 |
| EP | 0371838 | A1 | 6/1990 |
| WO | WO-9501198 | A1 | 1/1995 |
| WO | WO-2008086552 | A2 | 7/2008 |
| WO | WO-2009016638 | A1 | 2/2009 |
| WO | WO-2009033032 | A1 | 3/2009 |

OTHER PUBLICATIONS

WO 2009/016,638, Yodfat, publication date: Feb. 5, 2009.*

(Continued)

*Primary Examiner* — Manuel Mendez
(74) *Attorney, Agent, or Firm* — Roche Diagnostics Operations, Inc.

(57) ABSTRACT

Systems, methods and devices are described herein for adjusting the insertion depth of a cannula associated with a portable therapeutic device within the body of a patient. The systems may include a mounting unit securable to the skin of the patient and having a mounting base and a well defining a passageway through the mounting base and a cannula unit including a cannula subcutaneously insertable through the well of the mounting unit. The well may have an adjustable height and/or adjustable anchoring mechanisms that allow for varying and customized insertion depths of the cannula within the body of the patient.

23 Claims, 34 Drawing Sheets

(56) References Cited

OTHER PUBLICATIONS

International Search Report for International Application No. PCT/IL2010/000887, date of mailing: Mar. 9, 2011.

Written Opinion of the International Searching Authority for International Application No. PCT/IL2010/000887, date of mailing: Mar. 9, 2011.

Patent Examination Report No. 1, Australian Patent Application No. 2010310941, date of issue: Nov. 2, 2012.

* cited by examiner 80
812
814
962
922
9622
921
96
9612
9614
961
50

SYSTEMS, METHODS AND DEVICES FOR ADJUSTING THE INSERTION DEPTH OF A CANNULA ASSOCIATED WITH A PORTABLE THERAPEUTIC DEVICE

CROSS-REFERENCE TO RELATED APPLICATIONS

The present application is a 35 U.S.C. §371 national stage entry of PCT/IL2010/000887, which has an international filing date of Oct. 28, 2010 and claims priority to U.S. Provisional Patent Application No. 61/256,326, filed on Oct. 30, 2009 and entitled "Adjustable Apparatus for Facilitating Infusion of Therapeutic Fluids and Sensing of Bodily Analytes," the disclosures of which are incorporated herein by reference in their entireties.

FIELD

The present disclosure relates generally to systems, methods and devices for administering therapeutic fluid into the body and/or sensing bodily analytes. Some embodiments of the present disclosure relate to a cannula and methods for securely inserting the cannula into the subcutaneous tissue of a patient's body. Some embodiments of the present disclosure relate to systems, methods and devices for securing a cannula to the patient's body and adjusting the depth to which the cannula is inserted into the patient.

BACKGROUND

Medically treating illnesses often requires delivering therapeutic fluid into various body compartments, such as the subcutaneous tissue. Diabetes mellitus patients, for example, require the administration of varying amounts of insulin throughout the day to control their blood glucose levels. Therapeutic fluid can be administered to the patient periodically as one or more daily fluid injections or continuously using infusion devices (e.g., an infusion pump). Subcutaneous injections are usually performed using a rigid (e.g., metal) hypodermic needle. Continuous fluid administrations are typically performed using a soft cannula that provides a passageway for fluid communication between, for example, subcutaneous tissue and an infusion device. A device that facilitates periodic (i.e., injections) and/or continuous fluid delivery without repeated needle or cannula insertion is described in International Publication No. WO 2009/016638 to Yodfat et al., the content of which is incorporated herein by reference in its entirety. Device embodiments described therein include a housing (also referred to as "mounting unit" or "mounting housing") that may be initially adhered to the skin of a patient and a cannula securable to the housing that may be inserted through a passageway provided in the housing into a subcutaneous compartment within the patient. The cannula may be initially assembled with an insertion needle extending through the cannula. After piercing the skin, the insertion needle may be retracted leaving the cannula in place in the patient's body. A fluid delivery device (e.g., a standard syringe, injection pen or infusion pump) may be coupled to the cannula to establish fluid communication between the fluid delivery device and the body of the patient.

When the fluid delivery device is an infusion pump, it is typically coupled to the cannula by some type of tubing (e.g., lengthy tubing external to the pump). The housing, cannula and tubing components (used in conjunction with the infusion pump) are usually referred to collectively as an "infusion set," as described, for example, in U.S. Pat. Nos. 4,755,173 to Konopka et al. and 5,522,803 to Teissen-Simony, the contents of which are incorporated herein by reference in their entirety. Infusion devices directly connectable to a housing without the use of tubing are disclosed, for example, in U.S. Patent Application Publication No. 2008/0215035 to Yodfat et al. and International Publication No. WO 2009/016638 to Yodfat et al., the contents of which are incorporated herein by reference in their entirety. Device embodiments disclosed in Publication No. 2008/0215035 include, for example, a skin-adherable housing configured as a cradle unit having a length and width substantially similar to that of the infusion device itself to facilitate removable connection of the infusion device to a patient. A connecting lumen provided in an outlet port of the infusion device may establish fluid communication between the device and a cannula connected to the cradle unit.

Another important aspect of medically treating and/or preventing illnesses includes the periodic and/or continuous monitoring or sensing of bodily analytes, such as glucose. Performing continuous and/or periodic sensing operations of bodily analytes within the interstitial fluid of the subcutaneous tissue is discussed, for example, in U.S. Pat. Nos. 5,390,671 to Lord et al. and 6,565,509 to Say et al., the contents of which are incorporated herein by reference in their entirety. Conventional sensing devices include a subcutaneous probe and a sensing unit that contains a processing unit. Insertion mechanisms and devices for subcutaneous probes are disclosed, for example, in U.S. Pat. No. 5,586,553 to Halili et al., the content of which is incorporated herein by reference in its entirety. The insertion set in Halili et al. includes a penetrating member extending through a mounting base adapted for seated mounting onto the patient's skin. A flexible probe includes a proximal segment carried by the mounting base and a distal segment protruding from the mounting base and having one or more electrodes thereon. When the mounting base is pressed onto the patient's skin, the penetrating member pierces the skin to subcutaneously place the probe's distal segment. The penetrating member can then be withdrawn from the mounting base, leaving the probe's distal segment within the patient's body. A device that facilitates both periodic and continuous sensing of a bodily analyte without repeated skin pricking is described, for example, in International Publication No. WO 2009/016638 to Yodfat et al.

SUMMARY

Embodiments disclosed herein relate to systems, methods and devices for adjusting the insertion depth of a cannula within the body of a patient. Such systems, methods and devices may be used in conjunction with various portable medical systems and devices, including without limitation, fluid delivery systems (e.g., infusion pumps) and analyte sensing devices. According to some embodiments of the present disclosure, a system that includes a mounting unit securable (e.g., adherable) to a patient's skin and a cannula unit having a cannula insertable into the patient's body through a passageway provided within the mounting unit is disclosed. In some embodiments, the cannula may be configured to be inserted subsequent to securing the mounting unit to the skin of the patient. In some embodiments, the cannula may be inserted simultaneously with securing the mounting unit to the patient's skin.

The cannula may be used to perform a variety of therapeutic functions, including without limitation, fluid delivery (e.g., to a subcutaneous tissue) and analyte sensing (e.g., in a subcutaneous tissue). As used herein, the term "cannula" may be interchangeably referred to as "probe" (i.e., the terms "cannula" and "probe" may be used interchangeably throughout the description and have the same meaning in the present application). In addition, as described herein, the terms "cannula" and "probe" may refer to a subcutaneously insertable member or element (e.g., a hollow tube or insertable rod) or a cannula unit (e.g., an assembly, unit or cartridge) that includes the cannula or probe itself, as well as additional components used in conjunction with the cannula or probe, including, for example, one or more of a hub, a self-sealing septum and a penetrating member.

According to some embodiments of the present disclosure, the mounting unit (or "mounting structure" or "mounting housing") may be tailored specifically to the patient's requirements such that a cannula having a fixed length can be inserted into the body at different depths, and/or cannulae having different lengths can be inserted into the body at the same (e.g., fixed) depth.

In some embodiments, the passageway provided within the skin-securable mounting unit is defined by a well. The well may include one or more anchoring mechanisms (e.g., latches) for securing the cannula unit to the mounting unit upon cannula insertion. The well, or at least a portion of the well, may protrude from the mounting unit's upper surface. In some embodiments, the well may be configured as a tubular projection. A portable therapeutic device, such as, for example, a fluid delivery device (e.g., a syringe, an injection pen or an infusion pump) and/or a bodily analyte sensing device, may be coupled to the mounting unit following insertion of the cannula into the body through the well.

In some embodiments, the height of the well may be adjusted to allow the user to insert the cannula at varying depths, as desired. The term "height of the well" may refer to the well's absolute height (i.e., the distance between the outer surface of the skin and an upper edge of the well) or the well's functional height (i.e., the distance between the outer surface of the skin and one or more of the anchoring mechanisms of the well which secure the cannula unit to the mounting unit).

In some embodiments, the well may have at least two parts or portions (e.g., a stationary part and a displaceable part). The two parts may be concentric and the displaceable part may be positioned within the stationary part (or vice versa). In some embodiments, the displaceable part may include the anchoring mechanisms (e.g., latches), such that displacement of the displaceable part relative to the stationary part dictates the functional height of the well. In some embodiments, displacement of the displaceable part relative to the stationary part may also determine the absolute height of the well.

In some embodiments, the well may include a plurality of sets of anchoring mechanisms positioned at different locations along the length of the well (i.e., at different heights relative to the bottom surface of the mounting base). The well may be configured such that only one set of anchoring mechanisms can be functional at a time (i.e., only one set captures and secures the cannula unit to the mounting unit). In some embodiments, the functional height of the well may be determined by whichever set of anchoring mechanisms is set to be the functional set. In some embodiments, setting a certain set of anchoring mechanisms to be functional may also dictate the absolute height of the well.

Some embodiments of the present disclosure may be directed to systems for adjusting the insertion depth of a cannula associated with a portable therapeutic device. System embodiments may include (i) a mounting unit securable to the skin of a patient and having a mounting base and a well defining a passageway through the mounting base and (ii) a cannula unit having a cannula subcutaneously insertable through the well of the mounting unit, wherein the well is adjustable to provide for varying insertion depths of the cannula within the body of the patient. The well may be integral with the mounting base or removably attached to the mounting base. Similarly, the cannula unit may be integral with the mounting unit or removably attached to the mounting unit. In some embodiments, the cannula unit may include a cannula hub attached to the cannula and having a self-sealable septum. Some system embodiments may be configured with a well having one or more folds akin to the bellows of an accordion, wherein stretching and/or compressing the one or more folds may alter the height of the well. In some embodiments, the well having the one or more folds may have at least one anchoring mechanism, which may be displaceable when the well is stretched and/or compressed. The well may also be provided at an oblique angle with respect to a contact surface of the mounting base that contacts the skin of the patient when the mounting base is secured to the skin of the patient, to enable insertion of the cannula at an oblique angle with respect to the skin of the patient. In some embodiments, the angle of the well relative to a contact surface of the mounting base that contacts the skin of the patient when the mounting base is secured to the skin of the patient may be adjustable to enable insertion of the cannula at varying angles.

Some system embodiments for adjusting the insertion depth of a cannula may include a mounting base having adhesive tape to secure the mounting unit to the skin of a patient. In some embodiments, the cannula may be adapted to deliver therapeutic fluid and/or sense a bodily analyte. System embodiments may be configured to receive a portable therapeutic device to enable performance of a therapeutic procedure (e.g., delivery of therapeutic fluid into the body of the patient and/or sensing a bodily analyte). The portable therapeutic device, in some embodiments, may include a fluid delivery device selected from the group consisting of a syringe, an injection pen and an infusion device (e.g., a single-part infusion device, a two-part infusion device) and/or also include a sensing device to sense bodily analytes.

In some system embodiments, the well may include a first part and a second part, where the second part may be displaceable relative to the first part. The second part may have one or more anchoring mechanisms for coupling the cannula unit to the mounting unit. In some embodiments, where the cannula unit is integral with the mounting unit, the cannula unit may be integral with the second part of the well. In some embodiments, the system (or, more specifically, the well) may be configured such that displacement of the second part relative to the first part alters the height of the well and/or displaces the one or more anchoring mechanisms. In some embodiments, the well may have a fixed height and be configured such that displacement of the second part relative to the first part may displace the one or more anchoring mechanisms within the well. In some embodiments, the second part may be configured for threaded engagement with the first part.

In some embodiments, the first part and the second part of the well may be substantially concentric and the second part of the well may be displaceable within the first part of the well. The first part may also include a plurality of threads disposed along at least a portion of the interior of the first part and the second part may include a plurality of threads disposed along at least a portion of the exterior of the second part, wherein the plurality of threads of the first part may be configured to interact with the plurality of threads of the second part to displace the second part relative to the first part. In some embodiments, the first part may be configured with at least one groove disposed along the interior of the first part and the second part may be configured with at least one protrusion disposed along the exterior of the second part, wherein the at least one protrusion of the second part is configured to be received within the at least one groove of the first part to displace the second part relative to the first part. In some embodiments, the first part of the well and the second part of the well may be substantially concentric and the second part may be displaceable externally to the first part. In some such embodiments, the first part may include a plurality of threads disposed along at least a portion of its exterior and the second part may include a plurality of threads disposed along at least a portion of its interior, such that the plurality of external threads of the first part may interact with the plurality of internal threads of the second part to displace the second part relative to the first part.

Some system embodiments may include a displacing tool configured to be coupled to the second part of the well and displace the second part relative to the first part of the well. The displacing tool may include one or more protrusions that engage with one or more corresponding recesses in the second part and/or may be configured to engage with the one or more anchoring mechanisms of the second part. In some embodiments, the displacing tool may be configured as a rod.

According to some embodiments, the well may include at least one anchoring mechanism to enable coupling of the cannula unit to the mounting unit. In some embodiments, the at least one anchoring mechanism may include at least one latch receivable within at least one corresponding recess of the cannula unit. In some embodiments, a retaining component may be configured to be positioned over the least one anchoring mechanism to push the anchoring mechanism inwardly and/or to prevent the anchoring mechanism from being pushed outwardly from the well to enable the coupling of the cannula unit to the mounting unit. The anchoring mechanism may include a plurality of sets of anchoring mechanisms, wherein each set of the plurality of sets of anchoring mechanisms includes one or more anchoring mechanisms. In system embodiments including a retaining component, the retaining component may be configured to be positioned over one set of anchoring mechanisms at a time.

Some embodiments of the present disclosure may be generally directed to a system for adjusting the insertion depth of an insertable element associated with a portable therapeutic device. Some system embodiments may include a mounting unit securable to the skin of a patient and having a mounting base and a well defining a passageway through the mounting base. In some embodiments, the system may further include a cartridge unit including an insertable element for subcutaneous insertion through the well of the mounting unit. The insertable element may be configured to deliver therapeutic fluid into the body of the patient and/or to sense a bodily analyte. In some embodiments, the well may be adjustable to allow varying insertion depths of the insertable element within the body of the patient.

Some embodiments of the present disclosure may be directed to methods for adjusting the insertion depth of a cannula within the body of a patient. Such methods may include securing a mounting unit to the skin of a patient. The mounting unit may have a mounting base and a well defining a passageway providing access to an area of the skin of the patient.

Method embodiments may also include adjusting the well to provide for a desired insertion depth of the cannula within the body of the patient. Method embodiments may further include inserting the cannula through the well and into the body of the patient. In some embodiments, adjusting the well may include displacing a second part of the well relative to a first part of the well and/or enabling one set of a plurality of sets of anchoring mechanisms to engage a cannula hub connected to the cannula. In some embodiments, the enabling step may include (i) positioning a retaining component over the one set of anchoring mechanisms to at least one of push the anchoring mechanisms inwardly and prevent the anchoring mechanisms from being pushed outwardly from the well, and/or (ii) pivoting inwardly at least a portion of the well having the one set of anchoring mechanisms. In some method embodiments, at least a portion of the well may be configured with one or more folds akin to the bellows of an accordion, wherein adjusting the well includes compressing and/or stretching the one or more folds. Some method embodiments may include coupling the well to the mounting base.

The present disclosure may further be directed to systems (e.g., mounting systems) for use with a portable therapeutic device. System embodiments may include (i) a mounting unit securable to the skin of a patient and having a mounting base and a well defining a passageway through the mounting base and (ii) a cartridge unit (e.g., cannula unit) having an insertable element (e.g., cannula) subcutaneously insertable through the well of the mounting unit, wherein the well is adjustable to provide for varying insertion depths of the insertable element within the body of the patient.

The present disclosure also provides for embodiments of an infusion port assembly for use with an infusion device. The assembly may comprise a mounting base adherable to the skin of a patient and a well defining a passageway provided within the mounting base. The assembly may further comprise a cannula insertable through the well. In some embodiments, the well is configured to allow varying insertion depths of the cannula within the body of the patient.

It is worth noting, that features described in any one or another of the embodiments described above and in the detailed description of disclosure which follows, may be combined, mixed and/or matched with one or another of the disclosed embodiments, and included features thereof.

BRIEF DESCRIPTION OF THE DRAWINGS

Some of the embodiments of the present disclosure are described with reference to the accompanying drawings. In the drawings, like reference numbers may indicate identical or functionally similar elements.

DETAILED DESCRIPTION

The subject matter described herein relates to devices, systems and methods for adjusting the insertion depth of a cannula within the body of a patient or user. The terms "patient" and "user" are used interchangeably throughout this disclosure.

Figure 1A:
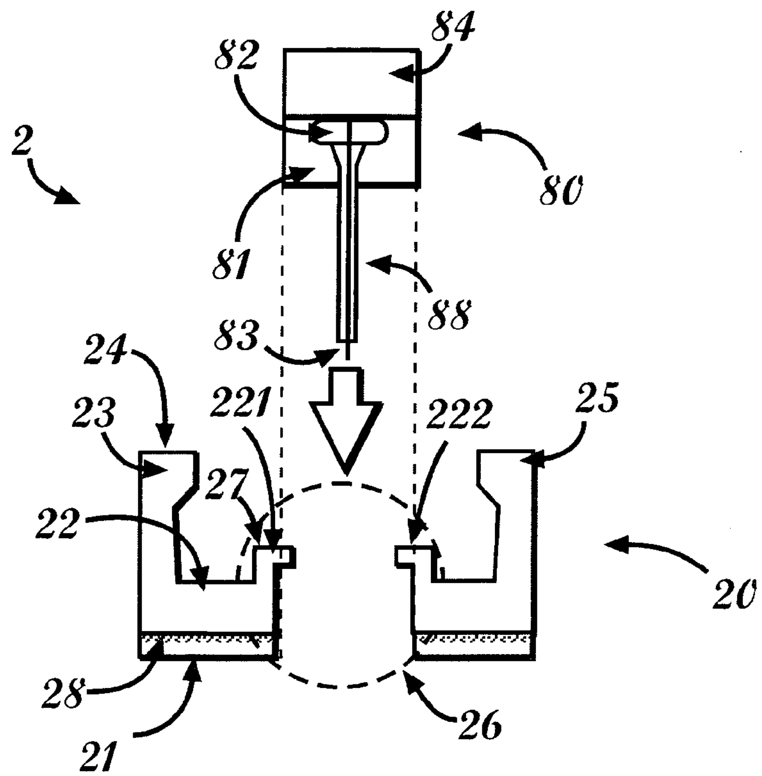
FIGS. 1*a*-1*c* show a mounting assembly having a skin-securable mounting unit and a cannula unit according to some embodiments of the disclosure.

Referring to FIG. 1*a*, a schematic diagram of a mounting assembly (or "mounting system") 2, which according to some embodiments may include a skin-securable (e.g., adherable) mounting unit 20 and a cannula unit 80, is shown. The mounting unit 20 may be configured to enable coupling, connecting and/or mounting of a therapeutic device thereon. Such a therapeutic device may be a device for delivering therapeutic fluid (e.g., insulin) into the body of a patient and/or for sensing concentration levels of bodily analytes (e.g., glucose). In some embodiments, the cannula unit 80 may include a cannula 88 and a cannula hub 81, which may be attached to the cannula 88 and may contain a self-sealable septum 82. The cannula unit 80 may further include a penetrating member 83 (e.g., an insertion needle) and a grip portion 84. In some embodiments, the mounting unit 20 may include a mounting base 22 and a passageway (e.g., a tubular passageway) defined by a well 26 to enable penetration of the cannula 88 through the mounting unit 20 and into the body. In some embodiments, the well 26 may be unitary with the mounting base 22. In some embodiments, the well 26 may be a separate unit connectable to the mounting base 22, as disclosed, for example, in U.S. Patent Application Publication No. 2008/0215035 to Yodfat et al., the content of which is incorporated herein by reference in its entirety.

The well 26, or at least a portion of the well 26, may protrude from an upper surface 24 of the mounting base 22. In some embodiments, an upper edge 27 of the well 26 is aligned with the upper surface 24 of the mounting base 22. The well 26 may include one or more anchoring mechanisms (e.g., latches) 221, 222 to engage the cannula unit 80 (e.g., the cannula hub 81 of the cannula unit 80) with the mounting unit 20 when the cannula 88 is being inserted through the mounting unit 20 and into the body. The anchoring mechanisms 221, 222 may include any suitable material, including plastic, vinyl and/or any other polymer-based substance. The mechanisms 221, 222 may have any stiffness (i.e., structural rigidity) suitable for achieving a desired functionality, such as rigidly maintaining the cannula unit 80 within the well 26 of the mounting unit 20. The mounting unit 20 may also include an adhesive tape 21 fixed to a bottom surface 28 of the mounting base 22 (e.g., the surface contacting or closest to the skin of a patient) to enable adherence of the mounting unit 20 to the body. The cannula 88 may be inserted into the body through the well 26 subsequent to adherence of the mounting unit 20 to the skin or, in some embodiments, the cannula 88 may be integral with the mounting unit 20 or coupled to the mounting unit 20 via the well 26 prior to adherence of the mounting unit 20 to the skin, such that the cannula 88 is inserted into the body simultaneously with adhering the mounting unit 20 to the skin. In some embodiments, the mounting unit 20 may include one or more securing mechanisms (e.g., latches and/or magnets) 23, 25 to enable removable connection of, for example, a cannula insertion device ("inserter") and/or a therapeutic device (e.g., an infusion pump and/or sensing device) to the mounting assembly 2.

Figure 1B:
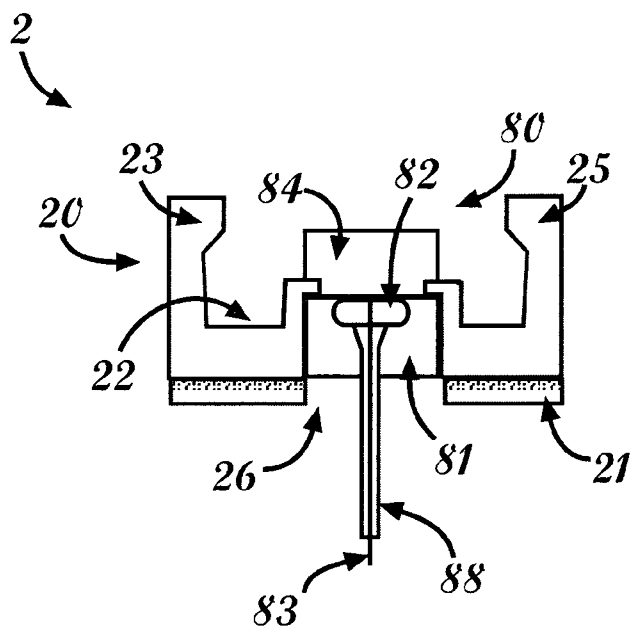
Figure 1C:
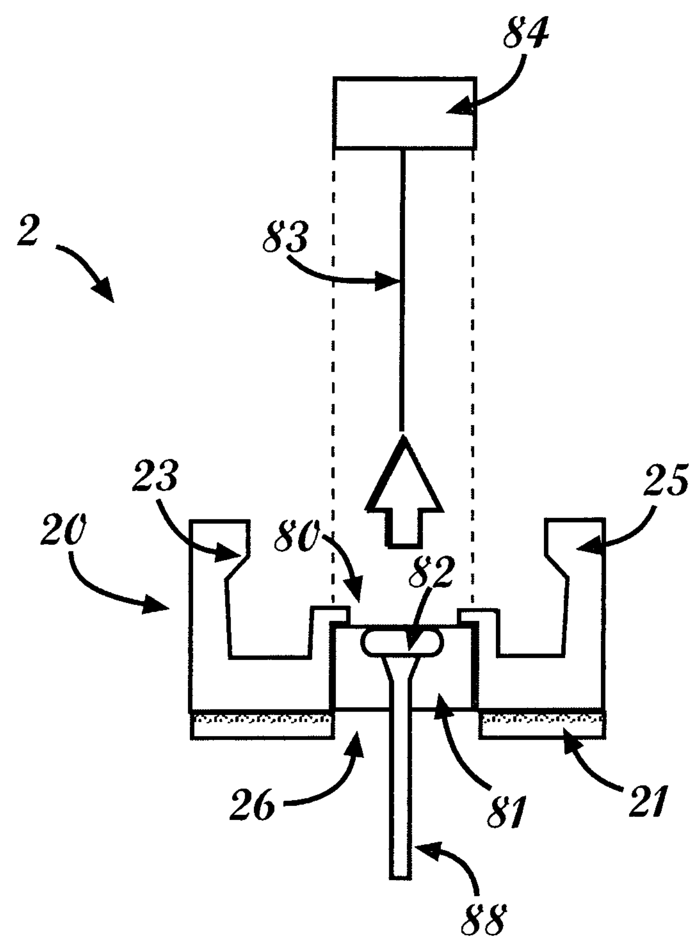

FIG. 1*b* depicts the mounting assembly 2 after coupling the cannula unit 80 to the mounting unit 20 and before removing the penetrating member 83 (FIG. 1*b*). FIG. 1*c* shows cannula unit 80 coupled with mounting unit 20 after removal of the penetrating member 83, whereby the cannula 88 is retained within the body. The cannula 88 may be inserted into the patient's body manually or using a dedicated inserter (not shown). In some embodiments, prior to coupling the cannula unit 80 to the mounting unit 20, the cannula unit 80 may be provided within a protective cover (i.e., a "protector"), as disclosed, for example, in U.S. Patent Application Publication No. 2008/0319416 to Yodfat et al., the content of which is incorporated herein by reference in its entirety. The cannula unit 80 with the protector may be loaded into an inserter, which may then be coupled to the mounting unit 20 for insertion of the cannula 88 into the body. Such inserters are disclosed, for example, in U.S. Patent Application Publication No. 2008/0319414 to Yodfat et al. and International Publication No. WO 2009/016638 to Yodfat et al., the contents of which are incorporated herein by reference in their entirety. In some embodiments, the cannula 88 may be inserted into the body at various angles with respect to the skin, (e.g., perpendicular to the skin or at an oblique angle to the skin). In some embodiments, the mounting assembly 2 may be configured as a single unit, where the cannula unit 80 and the mounting unit 20 are unitary. In such embodiments, the cannula 88 may be inserted into the body simultaneously with the adherence of the mounting unit 20 to the skin.

Figure 2:
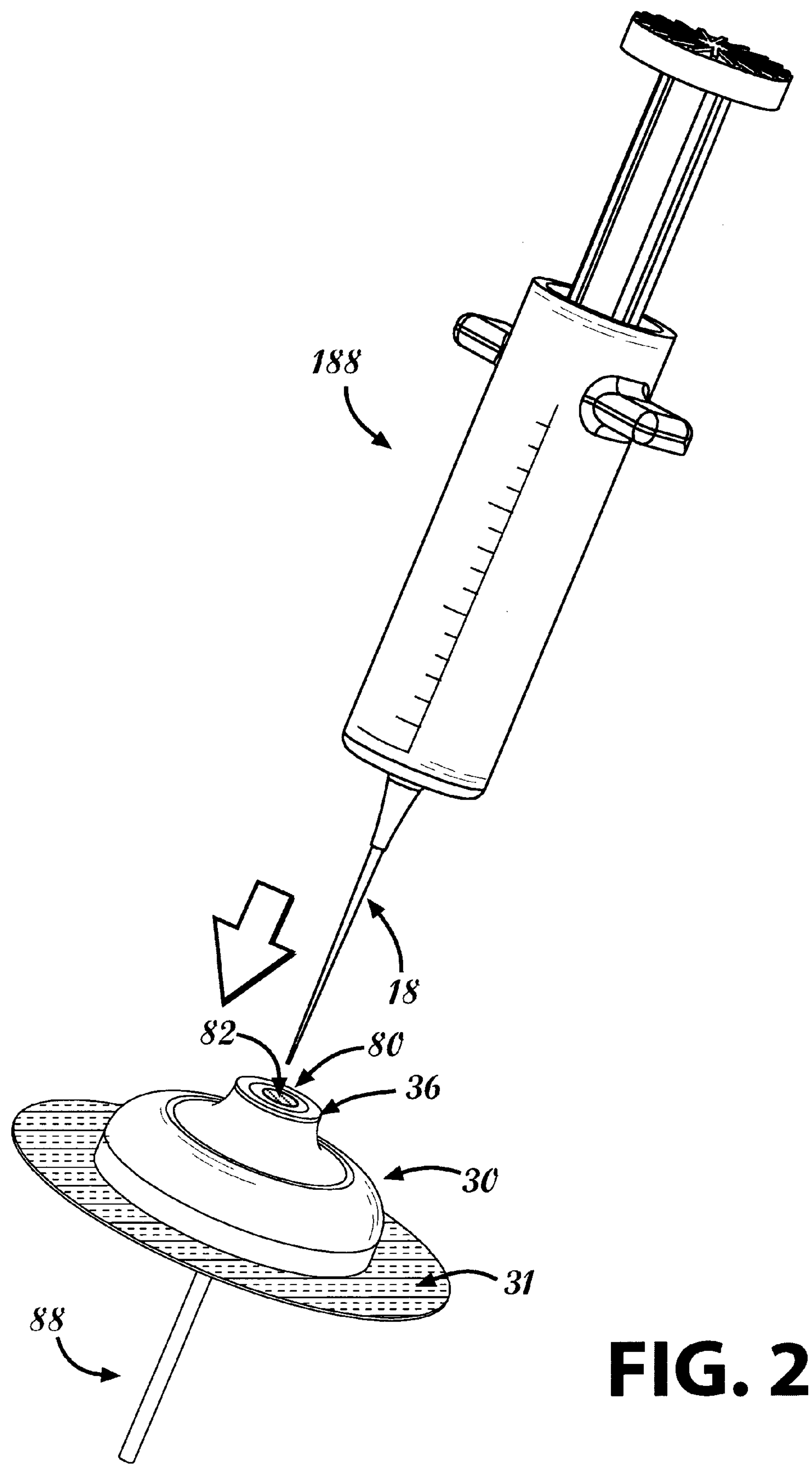
FIG. 2 shows a mounting unit configured as a port according to some embodiments of the disclosure.
Figure 3:
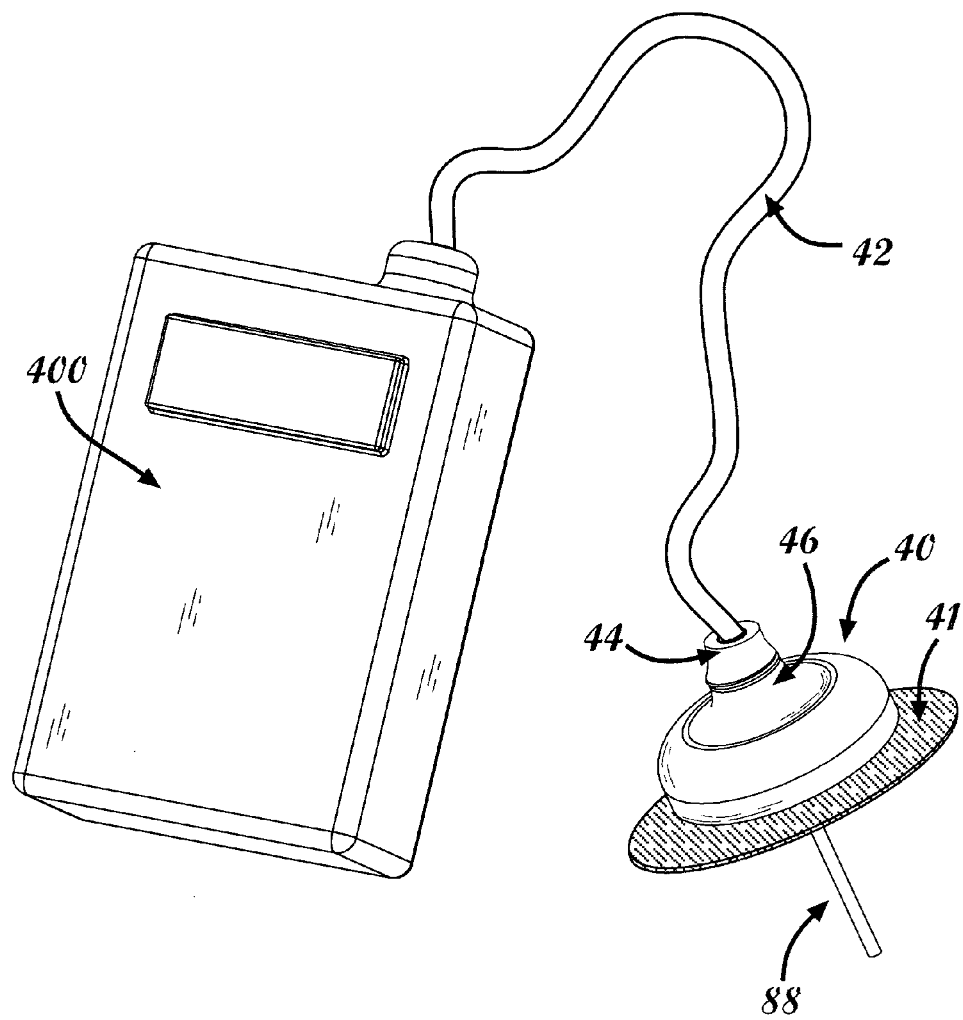
FIG. 3 shows a mounting unit configured as an infusion set port according to some embodiments of the disclosure.
Figure 4:
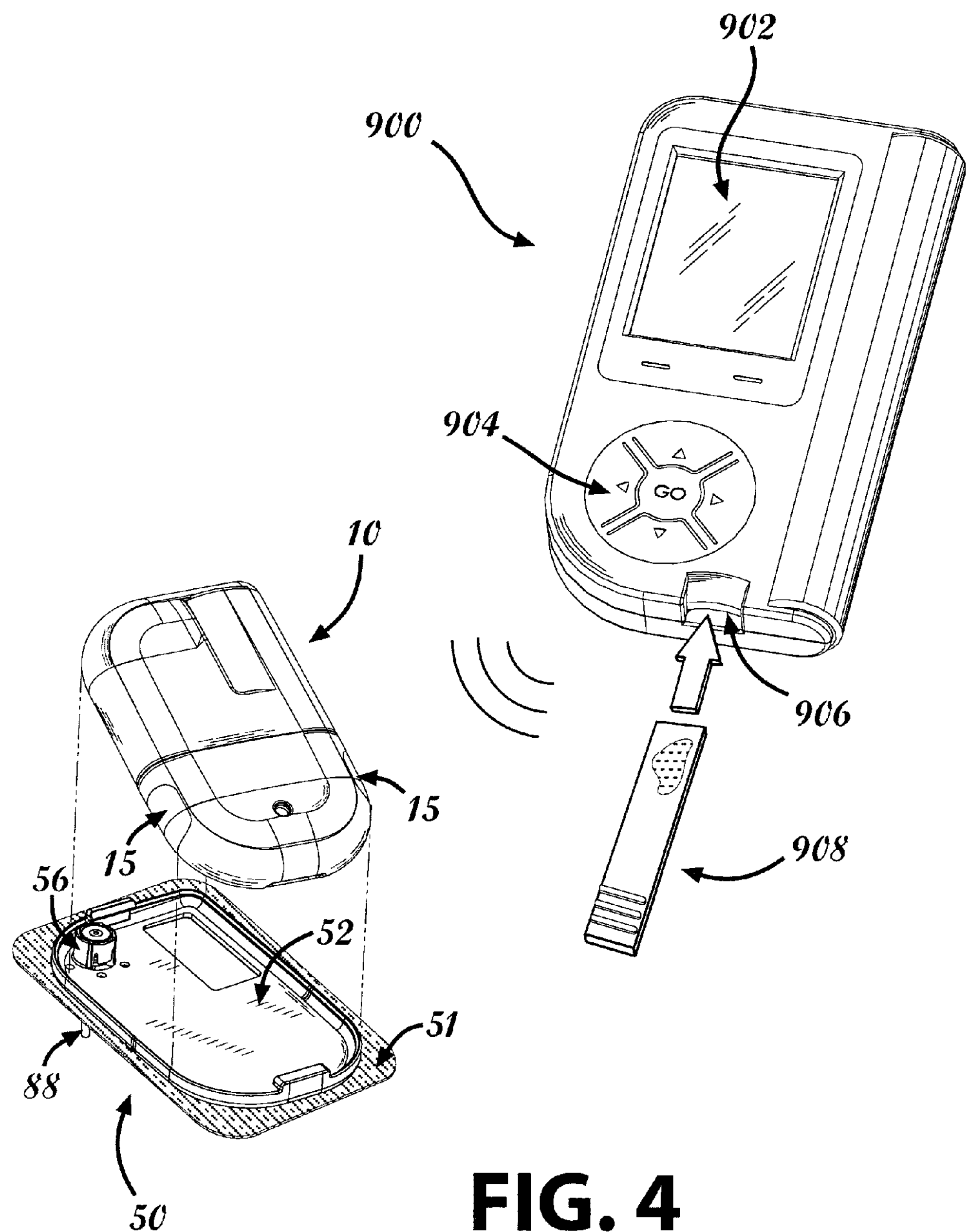
FIG. 4 shows a mounting unit configured as a cradle unit according to some embodiments of the disclosure.

FIGS. 2-4 show different types of mounting units which may be used in conjunction with a cannula unit. In some embodiments, the mounting units may include mechanisms for reducing the pain associated with skin pricking during insertion of a cannula into the body, or may be adapted to be used in conjunction with inserters which include mechanisms for reducing the pain associated with cannula insertion, as disclosed, for example, in International Publication Nos. WO 2009/001347 to Yodfat et al. and WO 2009/016638 to Yodfat et al., the contents of which are incorporated herein by reference in their entirety.

FIG. 2 shows a mounting unit 30 configured as a port for securely maintaining the attachment of a cannula to and within the body of a patient. In some embodiments, the port 30 may first be attached to a patient's skin (e.g., by virtue of an adhesive tape 31) and then the cannula unit 80 may be inserted through a passageway defined by a well 36 within the port 30. In some embodiments, the cannula unit 80 may be connected to the port 30 through the well 36 prior to attaching the port 30 to the skin. In some embodiments, the port 30 and the cannula unit 80 may be configured as a single integral unit. The port 30 may be configured, according to some embodiments, for releasable connection with a portable fluid delivery device, including without limitation, a syringe 188 or an injection pen (not shown). A self-sealable septum 82 (e.g., a rubber septum) sealing the well 36 can be repeatedly pierced by a needle 18 to establish fluid communication between the syringe 188, for example, and the cannula 88. A mounting unit configured as a port is disclosed in International Publication No. WO 2009/016638 to Yodfat et al., the content of which is incorporated herein by reference in its entirety.

FIG. 3 shows a mounting unit 40 configured as an infusion set port. In addition to the infusion set port 40, the infusion set may include a tube 42, a connector 44 and a cannula unit (only the cannula 88 is shown in FIG. 4). In some embodiments, the infusion set port 40 may be attached first to a patient's skin (e.g., by virtue of an adhesive layer 41) and then the cannula 88 may be subcutaneously inserted through a passageway defined by a well 46. In some embodiments, the infusion set port 40 and the cannula unit may be configured as a single integral unit, thus causing cannula 88 to be inserted simultaneously with the adherence of the infusion set port 40 to the skin. The connector 44 allows disconnection of an infusion pump 400 (e.g., a pager-type pump) and the tube 42 from the infusion set port 40 at the patient's discretion.

FIG. 4 shows a mounting unit 50 configured as a cradle unit or "cradle." The terms "cradle unit" and "cradle" are used interchangeably throughout this disclosure. In some embodiments, the cradle 50 may be adherable to the patient's skin (e.g., by virtue of an adhesive layer 51) and may include a cradle base 52 and a well 56 that defines a passageway for the insertion of cannula 88 through the cradle 50 and into the patient's body. In some embodiments, the well 56 may be structured as a protrusion extending radially (e.g., upwardly) from the cradle base 52 to enable alignment and appropriate connection of a therapeutic device 10 (e.g., an infusion pump and/or a sensing device) to the cradle 50 after insertion of the cannula 88. A device employing a cradle is described, for example, in the U.S. Patent Application Publication No. 2008/0215035 to Yodfat et al., the content of which is incorporated herein by reference in its entirety. The therapeutic device 10 may be controlled by a remote control unit 900 ("remote control") or using buttons and/or switches 15 located on the therapeutic device 10. In some embodiments, the remote control 900 may be configured as a handheld device for programming fluid flow profiles, controlling the therapeutic device 10, acquiring data and/or providing indications to a patient. As shown in FIG. 4, the remote control unit 900 may include a screen and/or display 902, a keypad 904 and a blood glucose monitor, depending on the embodiment. A test strip 908 may be received within a recess 906 in the remote control unit 900 to enable analyte (e.g., glucose) concentration levels to be evaluated and/or presented on the screen 902.

Figure 5A:
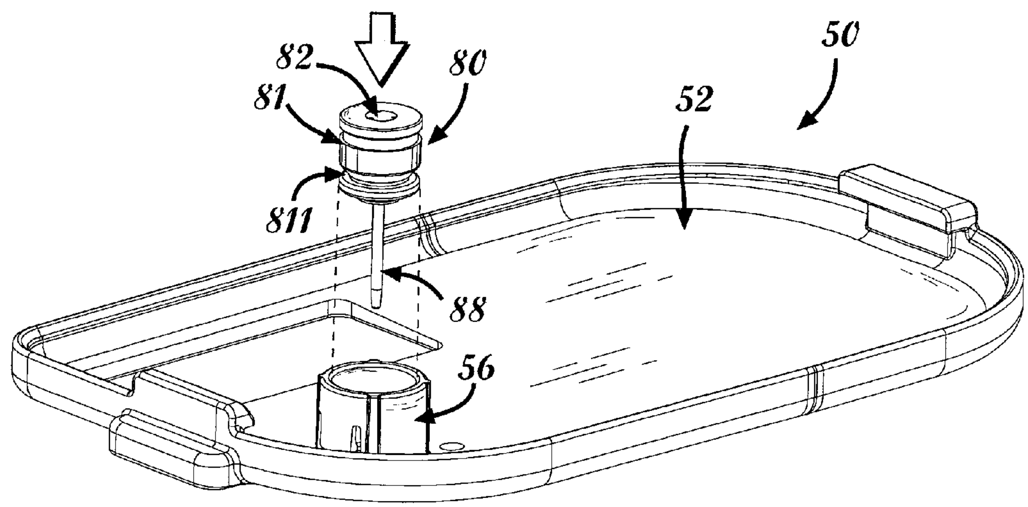
FIGS. 5*a*-5*b* show a cradle unit and a cannula unit before (FIG. 5*a*) and after (FIG. 5*b*) connection according to some embodiments of the disclosure.
Figure 5B:
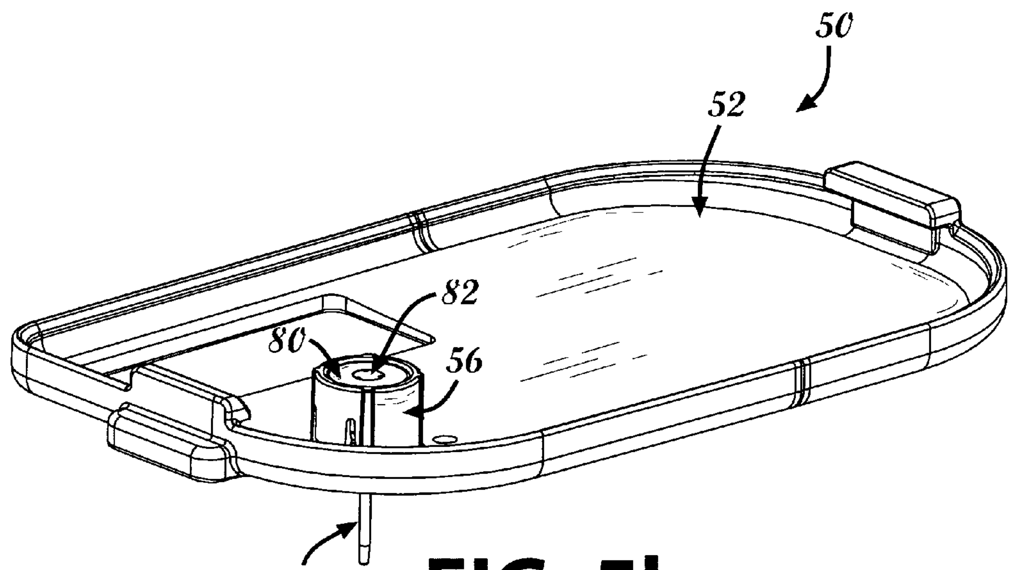

FIG. 5*a* shows cradle 50 and cannula unit 80 prior to connection, according to some embodiments of the present disclosure. In some embodiments, the cannula unit 80 may include a cannula 88 and a cannula hub 81 which may be attachable to the cannula 88 and contain a self-sealable septum 82. The cannula hub 81 may include at least one recess and/or groove (e.g., an annular recess 811) for receiving at least one corresponding anchoring mechanism (not shown) of the well 56 and establishing a secure connection between the cannula unit 80 and the cradle 50. FIG. 5*b* shows an embodiment of the cradle 50 and the cannula unit 80 after connecting the cannula unit 80 within the well 56 of the cradle 50.

Figure 6A:
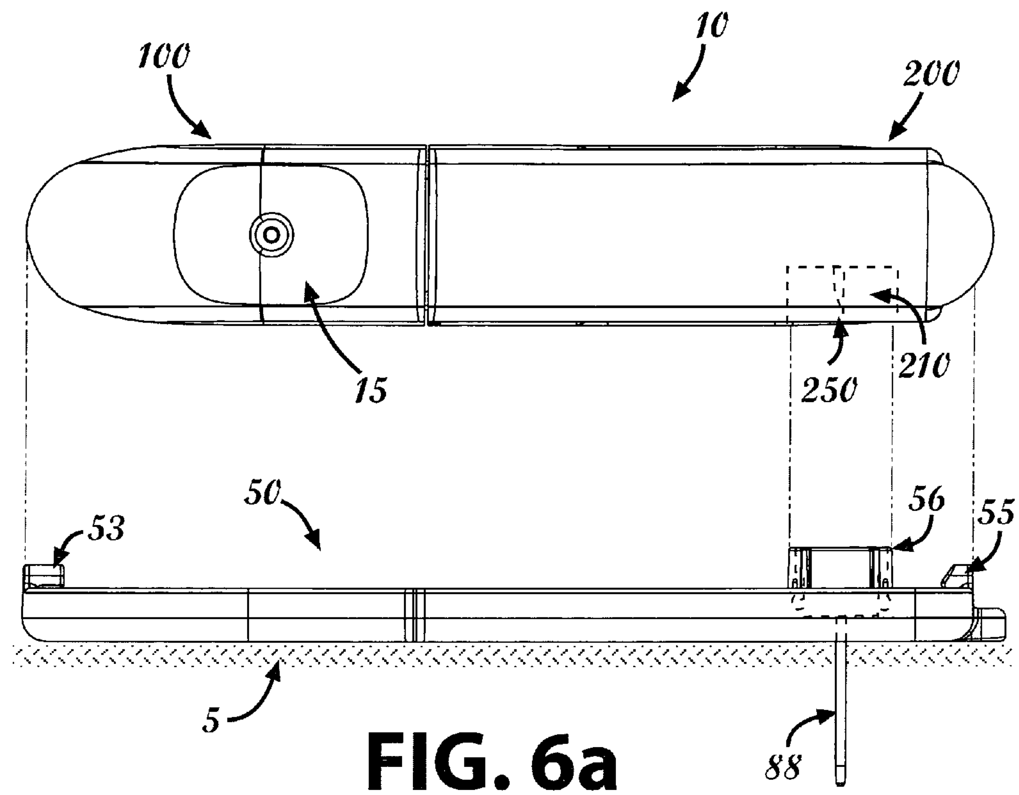
FIGS. 6*a*-6*b* show a two-part therapeutic device before (FIG. 6*a*) and after (FIG. 6*b*) connection to a cradle unit and cannula unit assembly according to some embodiments of the disclosure.
Figure 6B:
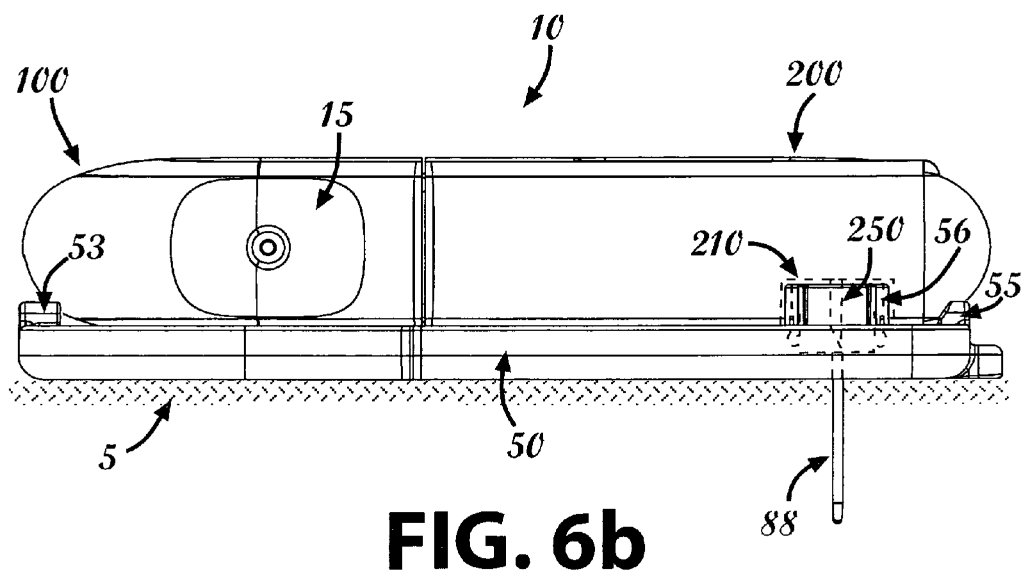

FIG. 6*a* shows a cradle 50 and a therapeutic device 10 prior to connection with one another. After securing (e.g., adhering) the cradle 50 to the skin 5 of a patient, a cannula 88 is subcutaneously inserted through the well 56. The therapeutic device 10 can then be connected to the cradle unit 50. The therapeutic device 10 may be composed of one or more parts. For example, in some embodiments, the therapeutic device 10 may include a reusable part 100 and a disposable part 200. As shown in FIG. 6*a*, the therapeutic device 10 may include an outlet port 210 at the bottom of the device 10. The outlet port 210 may include a connecting lumen 250 (e.g., a short needle), so that upon connection of the device 10 to the cradle 50, the outlet port 210 fits onto the well 56 and the connecting lumen 250 enables fluid communication between the device 10 and the cannula 88. In those embodiments where the therapeutic device 10 includes a reusable part 100 and a disposable part 200, the outlet port 210 and the connecting lumen 250 may be located on the bottom surface of the disposable part 200 of the device 10. According to some embodiments, the therapeutic device 10 may be disconnected from and reconnected to the cradle 50 at the patient's discretion. The cradle 50 may further include one or more securing mechanisms (e.g., latches) 53, 55 to secure the therapeutic device 10 to the cradle 50 and enable the disconnection and reconnection. FIG. 6*b* shows the cradle 50 and the therapeutic device 10 after connecting the therapeutic device 10 to the cradle 50.

Embodiments of the present disclosure may include a mounting unit having a passageway defined by a well, as described above. The height of the well, or at least a portion of the well, may be adjustable to allow a patient to choose the insertion depth of a cannula (e.g., in order to accommodate different fat layer thicknesses). In the present disclosure, the term "length of the cannula" (or "cannula length") refers to the length of that portion of the cannula which extends from the bottom of the cannula hub (see, e.g., 81 in FIG. 1) to the lower tip of the cannula 88.

Figure 7A:
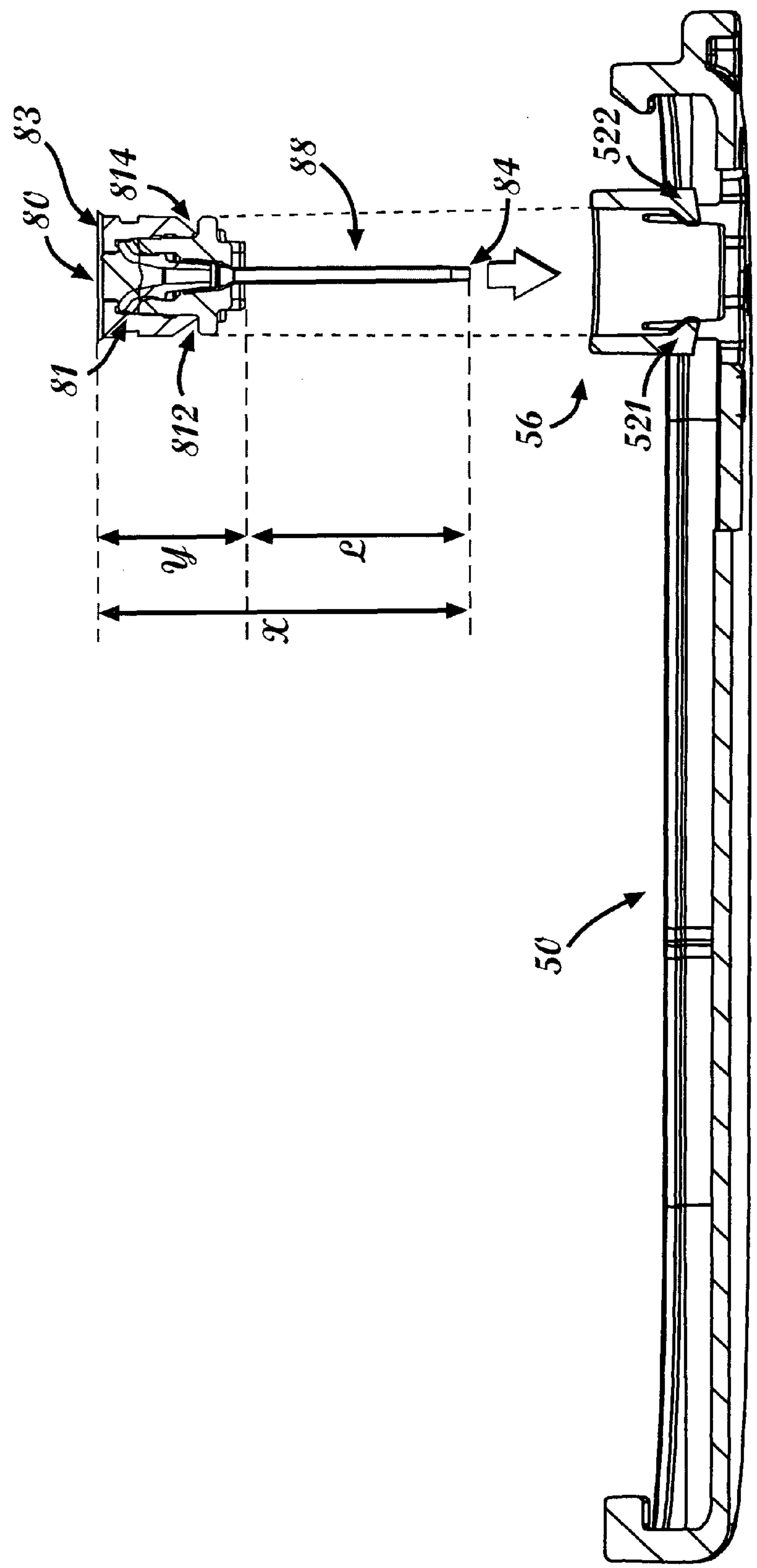
FIGS. 7*a*-7*d* show cross-sectional views of a cradle unit and cannula unit before (FIG. 7*a*) and after (FIGS. 7*b*-7*d*) connection that illustrate how the height of a well of the cradle unit may dictate the depth to which a cannula of the cannula unit is inserted into the body according to some embodiments of the disclosure.

FIG. 7*a* shows a cross-sectional view of a cradle 50 and a cannula unit 80 prior to connection. A cannula hub 81 may include recesses 812 and 814 (or a single annular recess, as shown in FIG. 5*a*) for receiving anchoring mechanisms (e.g., latches) 521, 522 of the well 56 and establishing a secure connection of the cannula unit 80 within the well 56. In some embodiments, the total length of the cannula unit 80 (i.e., the distance from the upper surface 83 of the cannula hub 81 to the tip 84 of the cannula 88) may be denoted as "X," the length of the cannula hub 81 may be denoted as "Y" and the length of the cannula 88 may be denoted as "L," such that L=X−Y.

Figure 7B:
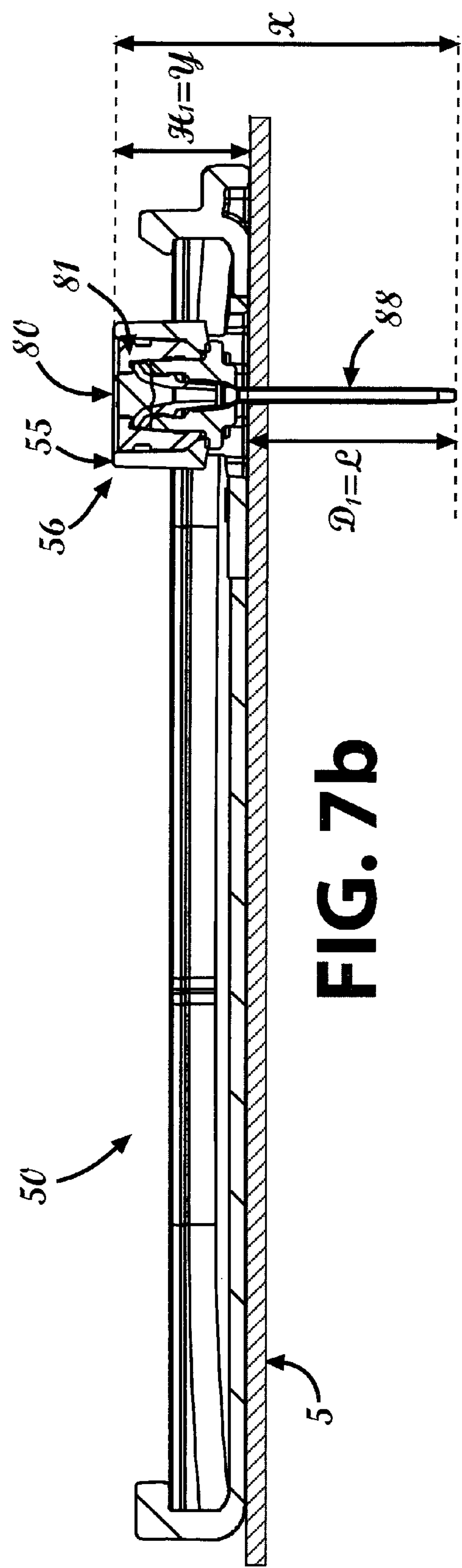
Figure 7C:
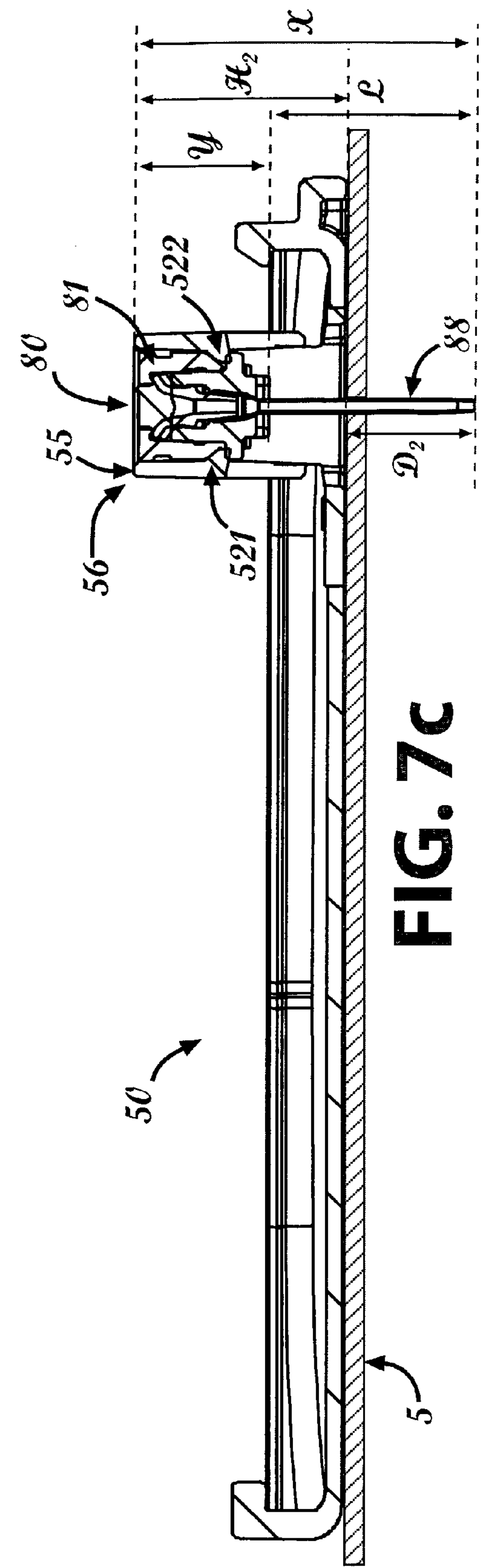
Figure 7D:
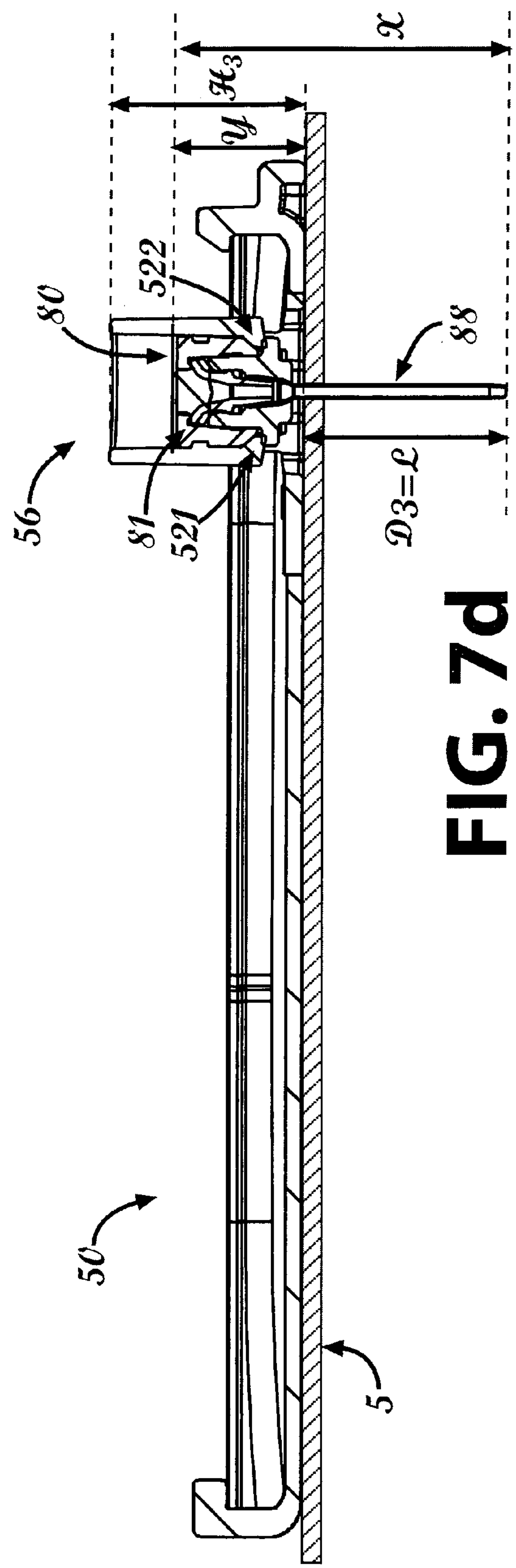

FIGS. 7*b*-7*d* demonstrate how the height of the well 56 (or the height of at least a portion of the well 56) can be used to dictate the depth to which the cannula 88, having a fixed length L, may be inserted into the body. Cross-sectional views of the cradle 50 and the cannula unit 80 connected thereto are shown in FIGS. 7*b*-7*d*. As used herein, the term "absolute height of the well" refers to the distance from the outer surface of the skin 5 (or the bottom surface of the cradle 50) to the upper edge 55 of the well 56. As used herein, the term "functional height of the well" refers to the distance from the outer surface of the skin 5 (or the bottom surface of the cradle 50) to the anchoring mechanisms 521, 522. In FIG. 7*b*, the absolute height $H_1$ of the well 56 substantially matches the length Y of the cannula hub 81, and the insertion depth $D_1$ of the cannula 88 substantially matches the length L of the cannula 88. In FIG. 7*c*, the absolute height $H_2$ of the well 56 is greater than the length Y of the cannula hub 81, and the insertion depth $D_2$ of the cannula 88 is smaller than the length L of the cannula 88. In some embodiments, the location of the anchoring mechanisms 521, 522 within the well 56 may be configured to prevent the cannula 88 from being inserted deeper into the body. Both the absolute height and the functional height of the well are greater in FIG. 7*c* than in FIG. 7*b*.

In FIG. 7*d*, the absolute height $H_3$ of the well 56 is larger than the length Y of the cannula hub 81 (e.g., $H_3=H_2$); however, the insertion depth $D_3$ of the cannula 88 substantially matches the length L of the cannula 88 (e.g., $D_3=D_1$). In some embodiments, while the absolute height of the well 56 may be fixed (i.e., nonadjustable and/or unchangeable), a portion of the well 56 may have displaceable anchoring mechanisms 521, 522 for adjusting the functional height of the well 56 to provide for a desired insertion depth of the cannula 88. In some embodiments, the absolute height of the well may be varied without changing the functional height of the well, as exemplified in FIGS. 7*b* and 7*d*.

FIGS. 8*a*-21*b* show exemplary mechanisms for adjusting the absolute height and/or functional height of a well of a cradle 50. In some embodiments, the absolute height of the well may fixed, such that only its functional height is adjustable. In some embodiments, both the functional height and the absolute height of the well may be adjustable. In some embodiments, the absolute height and the functional height of the well may be linked such that adjustment of the functional height of the well affects the absolute height of the well, or vice versa. In some embodiments, the patient may choose the extent of the adjustment (e.g., the absolute and/or functional height of the well may be set to be half way between the maximum absolute and/or functional height and the minimum absolute and/or functional height). In some embodiments, adjusting the well's height (functional and/or absolute) may be carried out manually. In some embodiments, adjusting the well's height (functional and/or absolute) may be carried out automatically, for example, by pressing a button and/or switch located on the mounting unit. The button and/or switch may be mechanical or electrical. The mounting unit may be provided with a power source and appropriate electronic components which enable the user to adjust the well's height using an electrical switch located on the mounting unit and/or using a remote control (e.g., the remote control unit 900 shown in FIG. 4).

The height adjustment mechanisms described herein are demonstrated in relation to a cradle as an example, however, they may be employed in any type of mounting system or mounting unit, including those embodiments described above (e.g., a port, infusion set port and/or cradle).

In some embodiments, the well may have two or more parts. In some embodiments, at least one part of the well may be displaceable relative to another part of the well, which may be substantially stationary. In some embodiments, the substantially stationary part of the well may be integral with the mounting base. In some embodiments, the well may be substantially cylindrical and comprise two concentric parts, where one part is positioned within the other part and one of the two parts (i.e., either the inner part or the external part) is displaceable relative to the other of the two parts. In some embodiments, the displaceable part may include anchoring mechanisms for securing a cannula unit within the well. In such embodiments, the displacement of the displaceable part will dictate the functional height of the well. In some embodiments, the displacement of the displaceable part may also dictate the absolute height of the well.

Figure 8A:
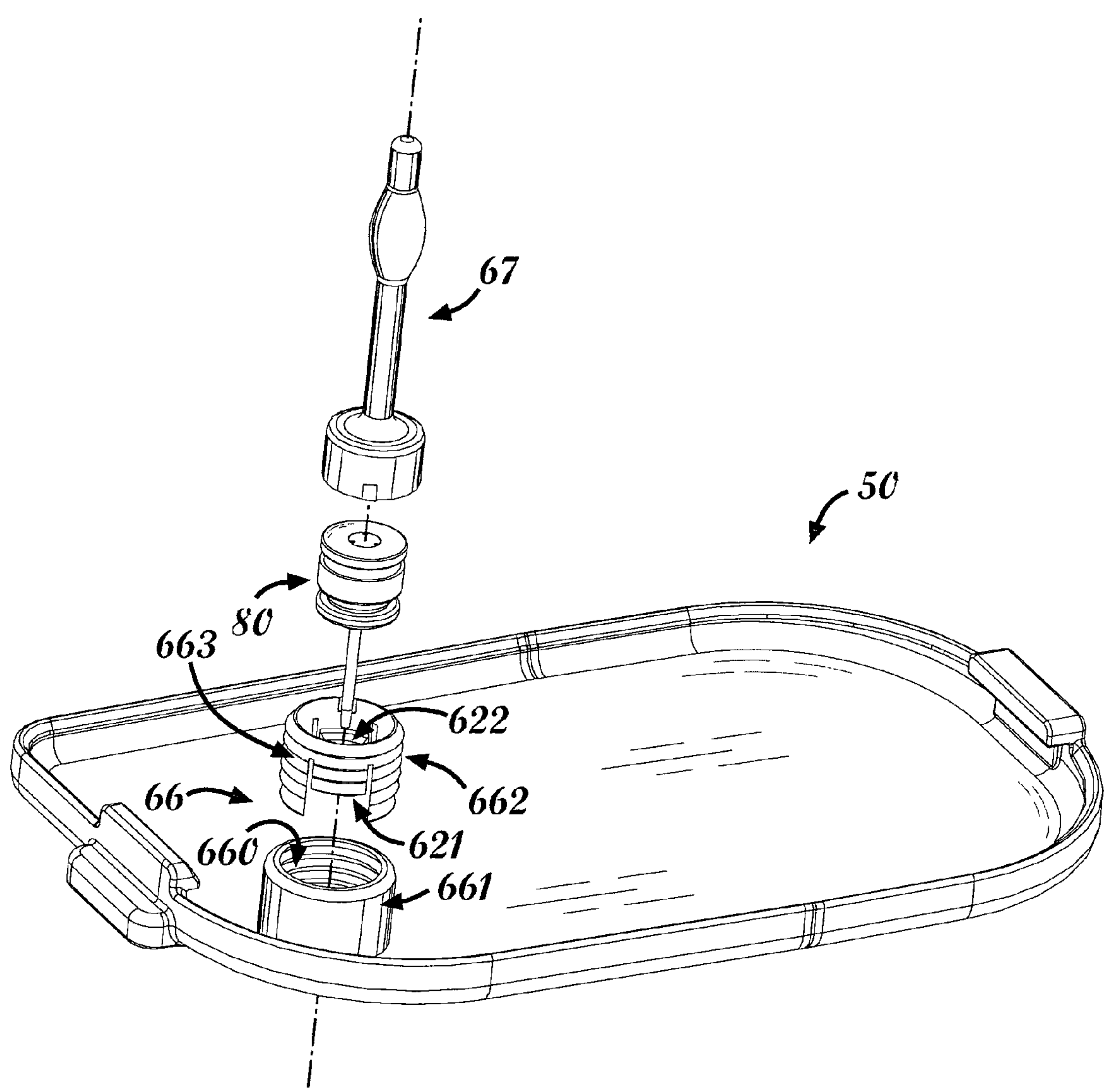
FIGS. 8*a*-9*d* show an embodiment of an adjustable mounting assembly in which both the functional height and the absolute height of a well of the cradle unit are adjustable according to some embodiments of the disclosure.
Figure 8B:
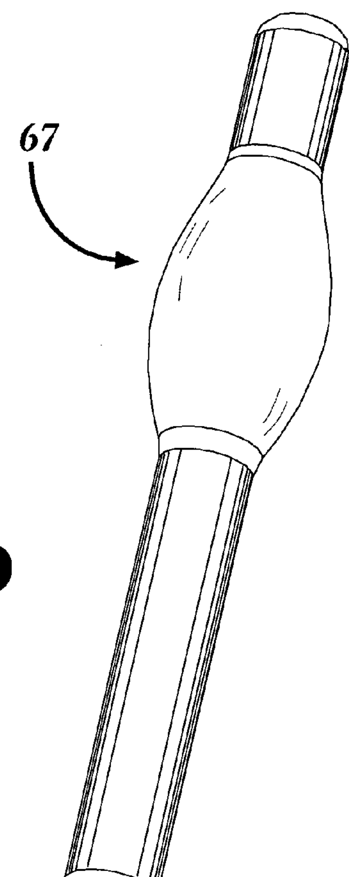
Figure 8C:
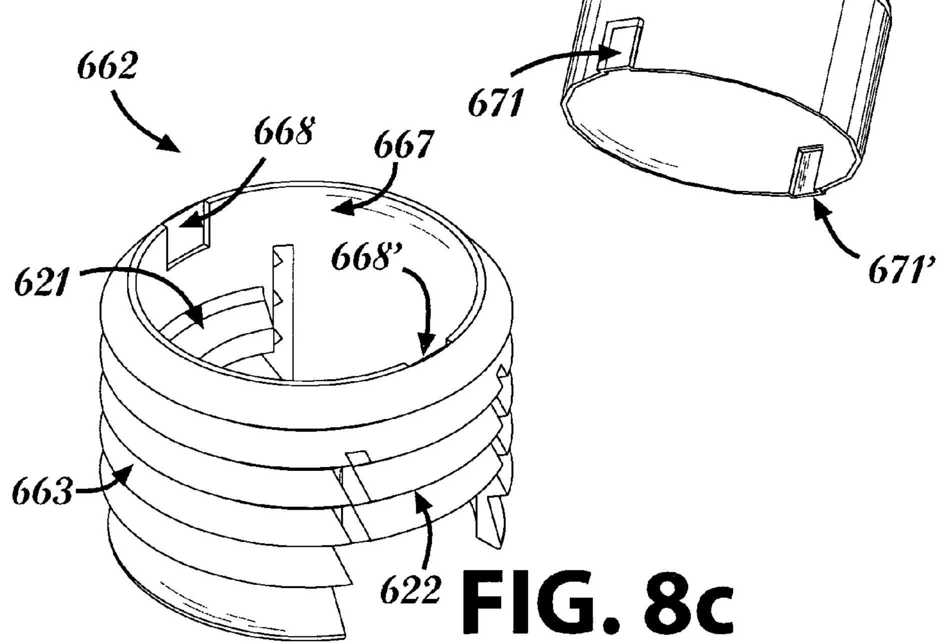

FIG. 8*a* shows an embodiment of a two-part well 66 having a screw-type height adjusting mechanism. In some embodiments, the well 66 may comprise a stationary part 661 and a displaceable part 662, which may include anchoring mechanisms 621, 622. The displaceable part 662 may be positioned within the stationary part 661 and, in some embodiments, the two parts 661, 662 may be concentric. In some embodiments, at least a portion of the external surface 663 of displaceable part 662 may be configured with external threads (e.g., external screw threads) and at least a portion of the internal surface 660 of stationary part 661 may be configured with corresponding internal threads that match the external threads of the displaceable part 662, as shown in FIG. 8*a*. In some embodiments, an auxiliary component, such as a rod 67, may be used to facilitate the displacement of the displaceable part 662 into and/or out of the stationary part 661 to adjust the absolute and/or functional height of the well 66. In some embodiments, the rod 67 may be coupled to the displaceable part 662 by one or more protrusions 671, 671', which may be configured to be received in corresponding one or more recesses (or grooves) 668, 668' located on an internal surface 667 of the displaceable part 662, as shown in FIGS. 8*b* and 8*c*. In some embodiments, the rod 67 may be coupled to the displaceable part 662 using the anchoring mechanisms (e.g., latches) 621, 622 or in any other way suitable for achieving displacement of the displaceable part 662 within stationary part 661. Adjusting the absolute and/or functional height of the well 66 may be carried out prior to connection of the cannula unit 80 to the well 66, either before or after adherence of the cradle 50 to the patient's skin. Alternatively, the absolute and/or functional height of the well may be adjusted following connection of the cannula unit 80 to the well 66, either before or after insertion of the cannula into the body, for example, when cannula insertion is simultaneous with adhering the cradle 50 to the skin or when a patient wishes to adjust the insertion depth of the cannula after cannula insertion to improve or eliminate associated discomfort. In some embodiments, the displaceable part 662 may be positioned externally to the stationary part 661. In such embodiments, the displaceable part 662 may be configured, at least in part, with internal threads and the stationary part may be configured, at least in part, with corresponding external threads.

FIGS. 9*a*-10*c* show an embodiment of a two-part well 66 having a screw-type height adjusting mechanism in which both the functional height and the absolute height of the well 66 are adjustable. In some embodiments, adjustment of either or both the functional and/or absolute height of the well 66 may be accomplished by threading displaceable part 662 into and/or out of stationary part 661 by rotating displaceable part 662 relative to stationary part 661. The displaceable part 662 may be rotated within stationary part 661 by using a tool (e.g., rod 67) or by a patient using his or her fingers.

Figure 9A:
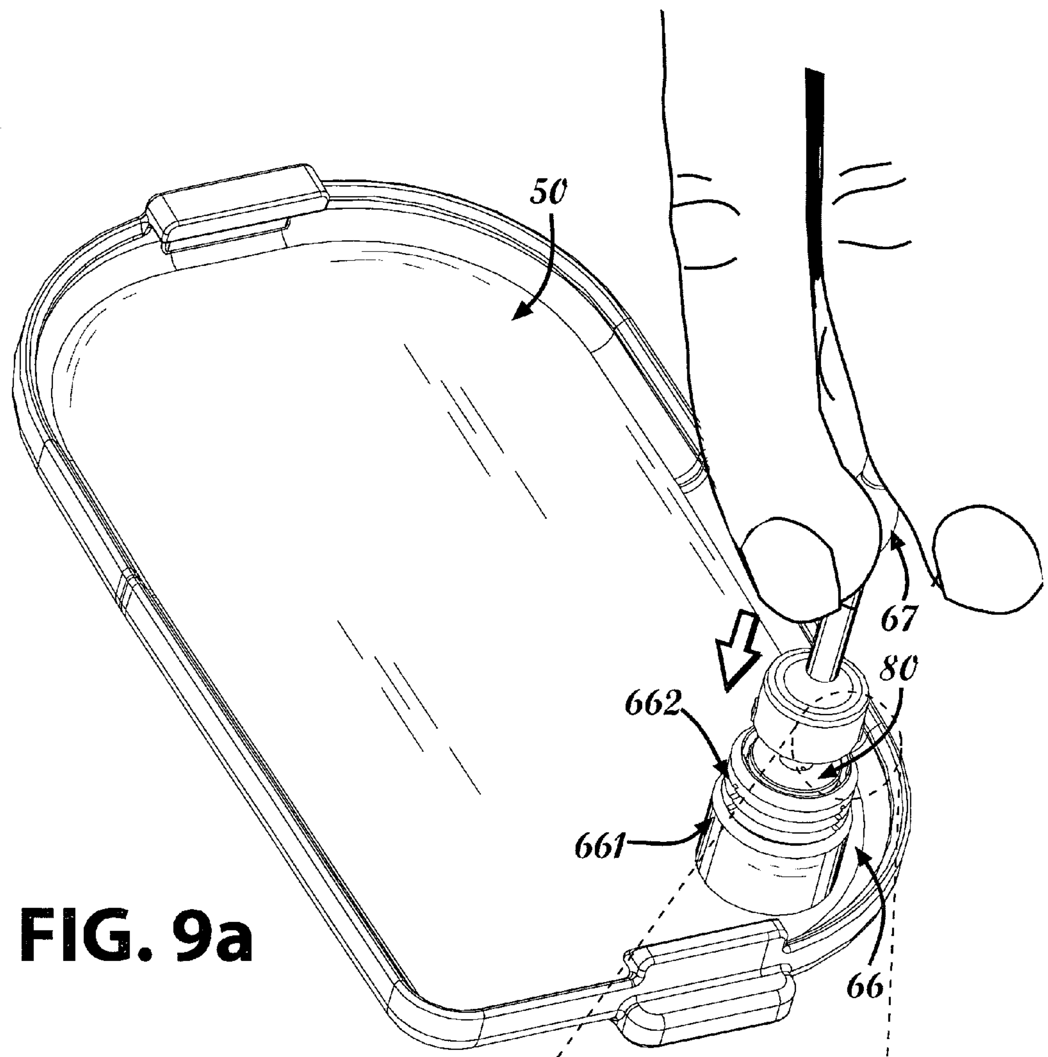
Figure 9B:
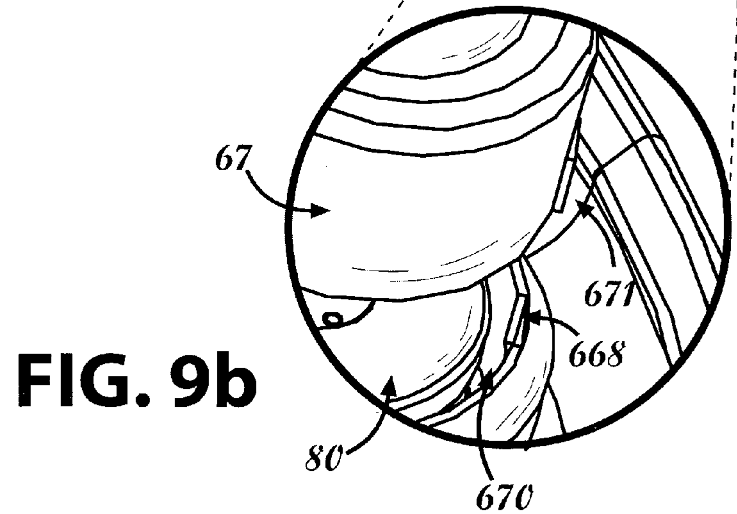
Figure 9C:
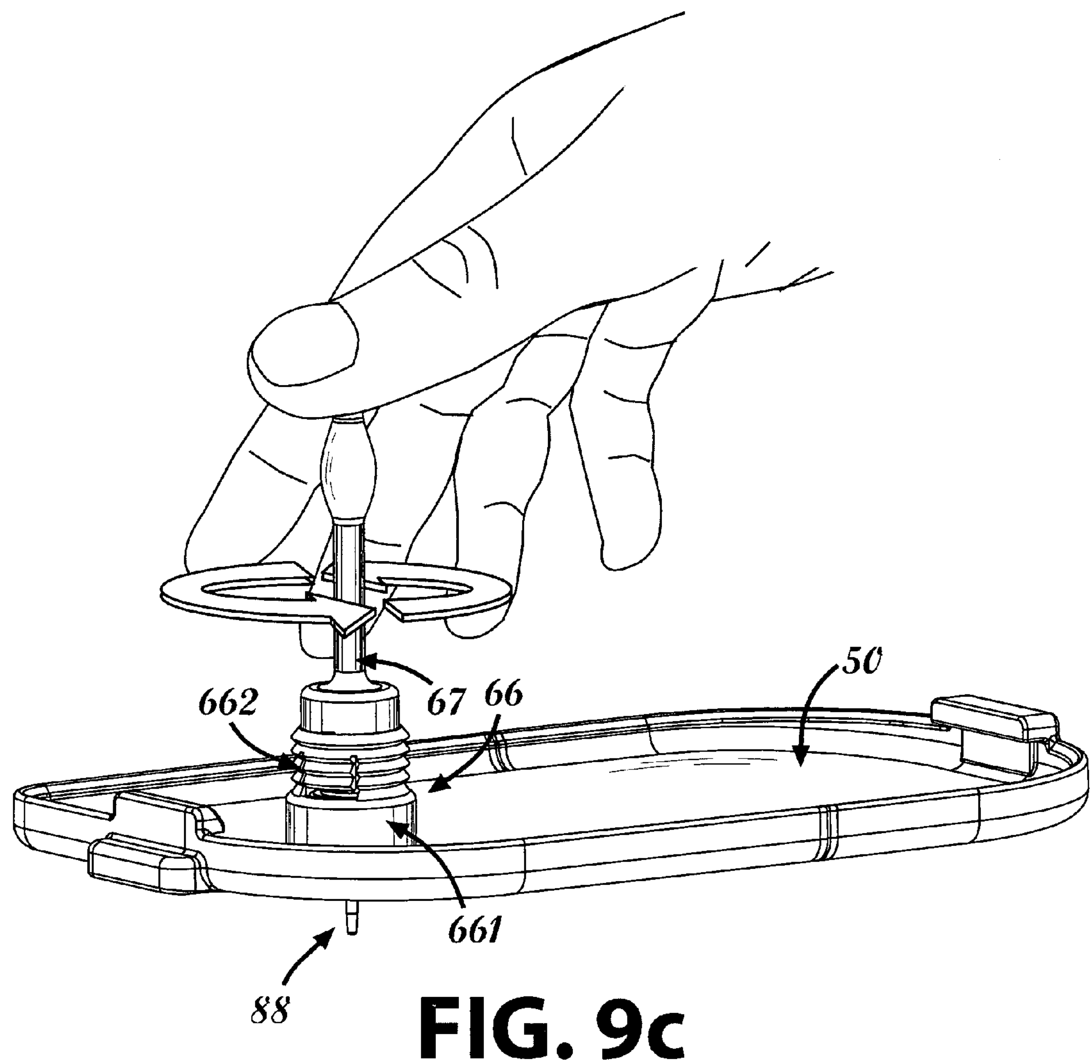
Figure 9D:
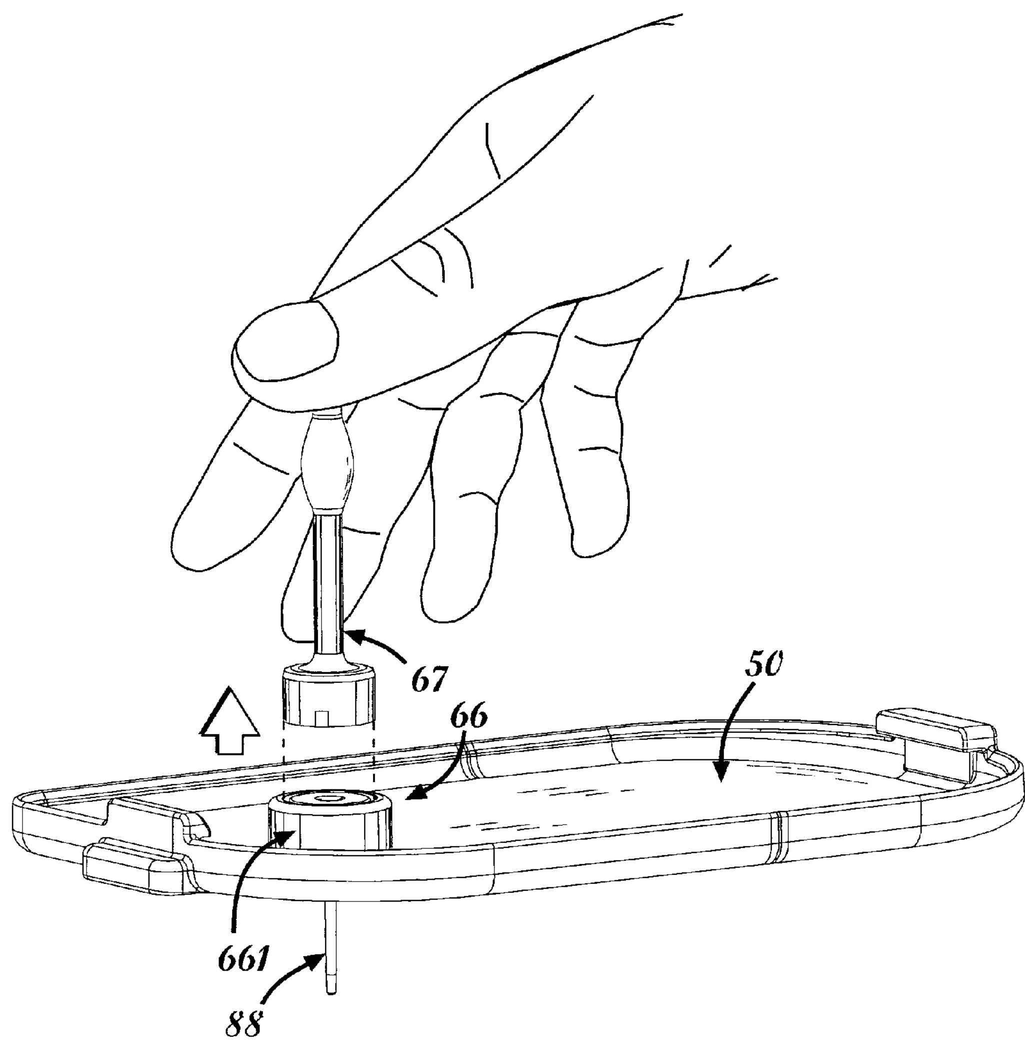

FIG. 9*a* shows a patient connecting rod 67 to displaceable part 662 of the well 66. In some embodiments, rod 67 may be connected to displaceable part 662 after cannula unit 80 is inserted within the well 66. As shown in FIG. 9*b*, the displaceable part 662 in some embodiments may be configured such that, when rod 67 is connected to displaceable part 662 after cannula unit 80 is inserted within the well 66, a space 670 exists between displaceable part 662 and cannula unit 80 to allow the patient to insert rod 67 into the well 66 until the protrusions 671 and 671' (only protrusion 671 is shown in FIG. 9*b*) of the rod 67 are received within the corresponding one or more recesses 668 and 668' (only recess 668 is shown in FIG. 9*b*) of the displaceable part 662. According to some embodiments, once protrusions 671 and 671' are positioned within the corresponding one or more recesses 668 and 668', the patient can use the rod 67 to rotate the displaceable part 662 into and/or out of stationary part 661, as shown in FIG. 9*c*. FIG. 9*d* shows the disconnection of the rod 67 from the well 66 after adjusting the well 66 to the desired absolute and/or functional height.

Figure 10A:
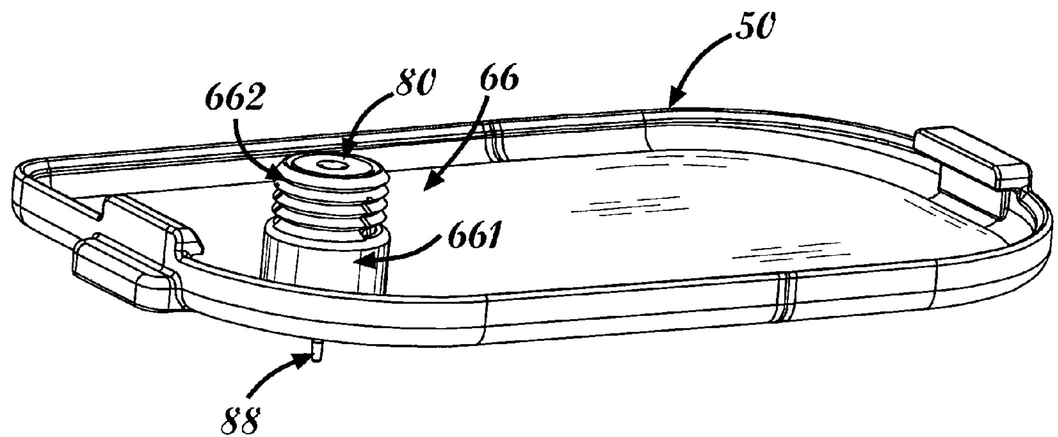
FIGS. 10*a*-10*c* show the well in FIGS. 8*a*-9*d* at a maximum functional height and maximum absolute height (FIGS. 10*a*, 10*c*) and at a minimum functional height and minimum absolute height (FIGS. 10*b*, 10*c*) according to some embodiments of the disclosure.
Figure 10B:
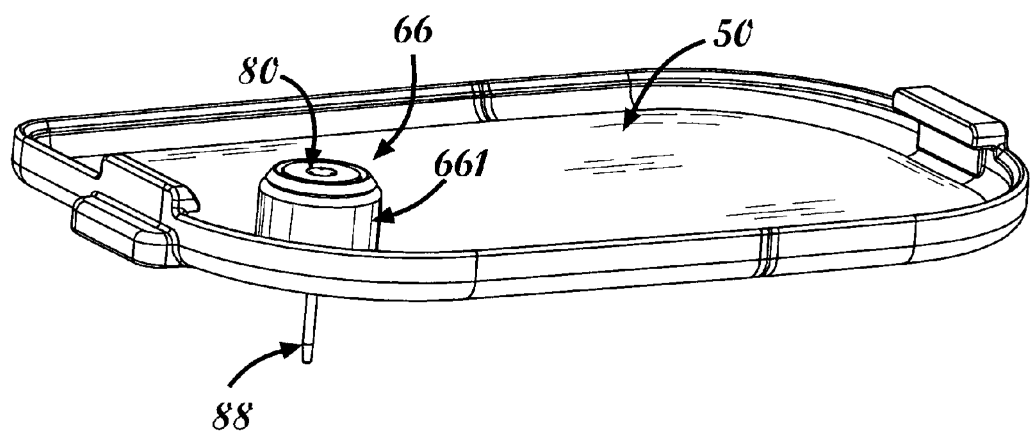
Figure 10C:
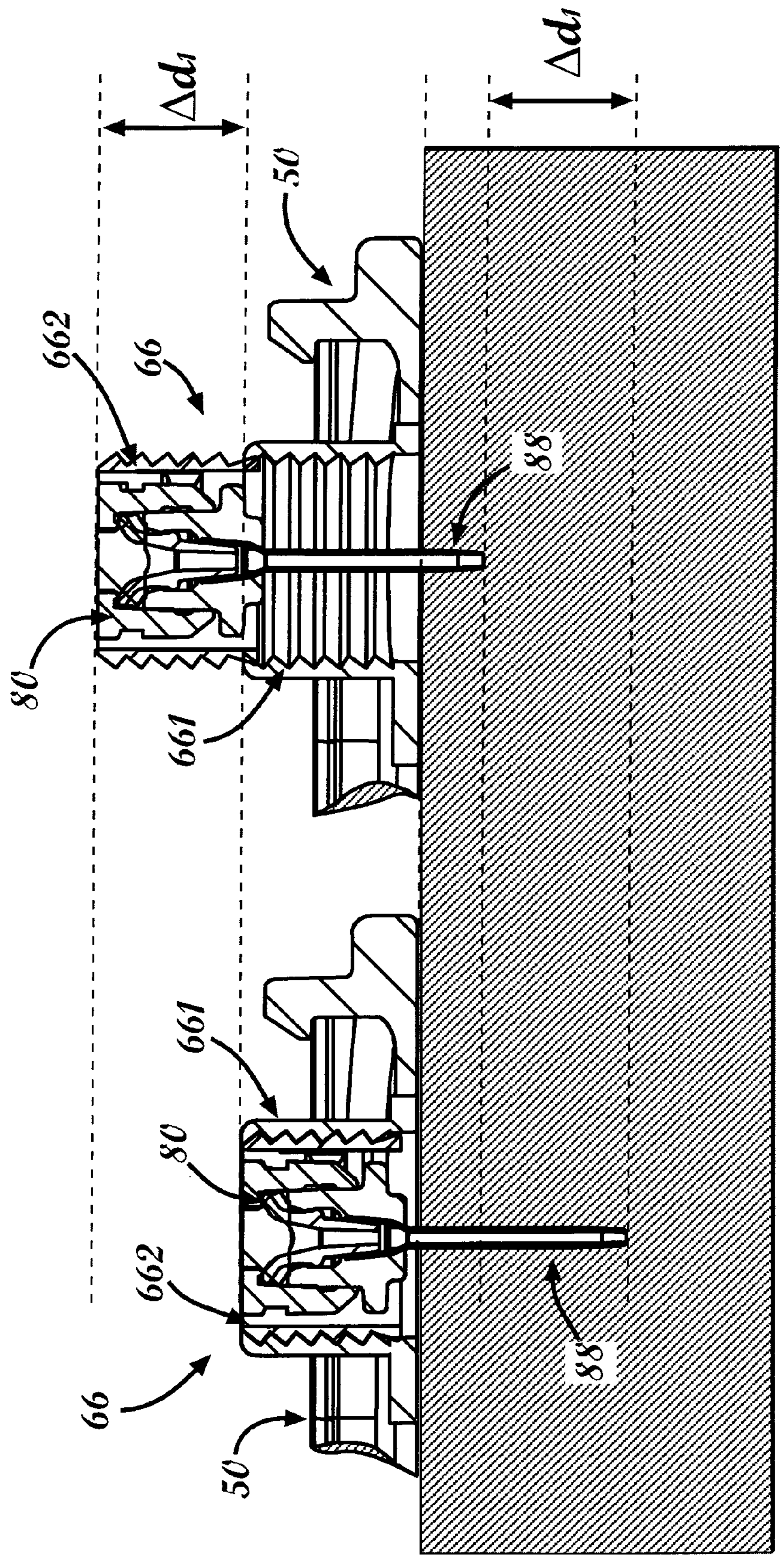

FIG. 10*a* shows an embodiment of the well 66 at a maximum functional and absolute height with cannula unit 80 inserted therein. FIG. 10*b* shows an embodiment of the well 66 after displaceable part 662 has been rotated into stationary part 661 to adjust the well 66 to a minimum functional and absolute height with the cannula unit 80 inserted therein. FIG. 10*c* shows a side-by-side comparison of the well 66 at a maximum functional and absolute height (on the right) and the well 66 at a minimum functional and absolute height (on the left). The change in positioning of the displaceable part 662 relative to the stationary part 661 (e.g., from maximum height to minimum height, as shown in FIGS. 10*a* and 10*b*) results in changes in insertion depth of the cannula 88 within the body. This change or difference in insertion depth (which corresponds to the "travel" distance of the displaceable part 662 out of the stationary part 661) is marked in FIG. 10*c* as "$\Delta d_1$".

FIGS. 11*a*-12*c* show an embodiment of a two-part well having a screw-type height adjusting mechanism in which only the functional height of the well 66 is adjustable. In the described and related embodiments, the absolute height of the well 66 may be fixed, e.g., by limiting the linear movement of the displaceable part 662 within the stationary part 661, such that the patient is able to adjust only the functional height of the well 66.

Figure 11A:
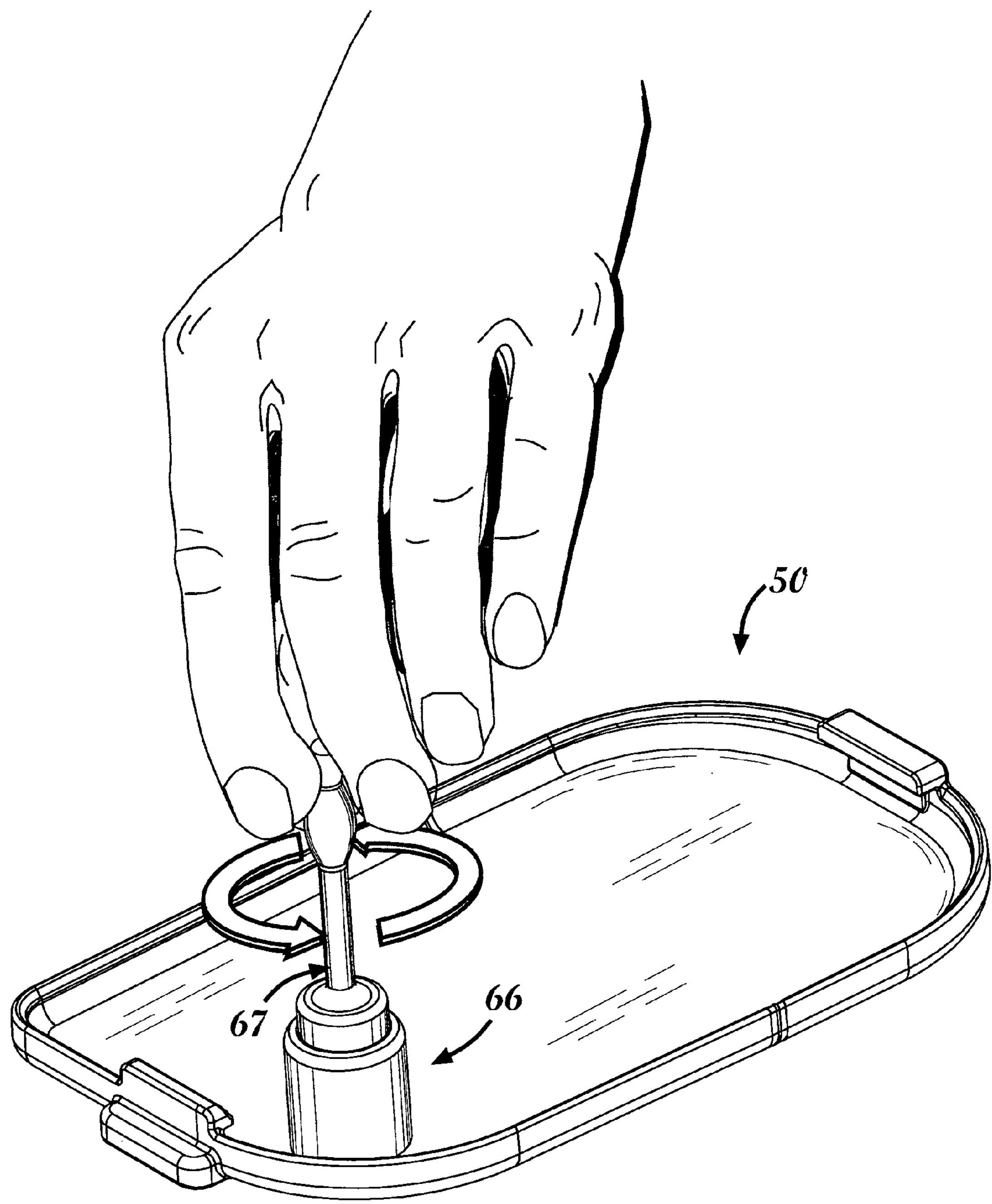
FIGS. 11*a*-11*b* show an embodiment of an adjustable mounting assembly in which only the functional height of a well of the cradle unit is adjustable according to some embodiments of the disclosure.
Figure 11B:
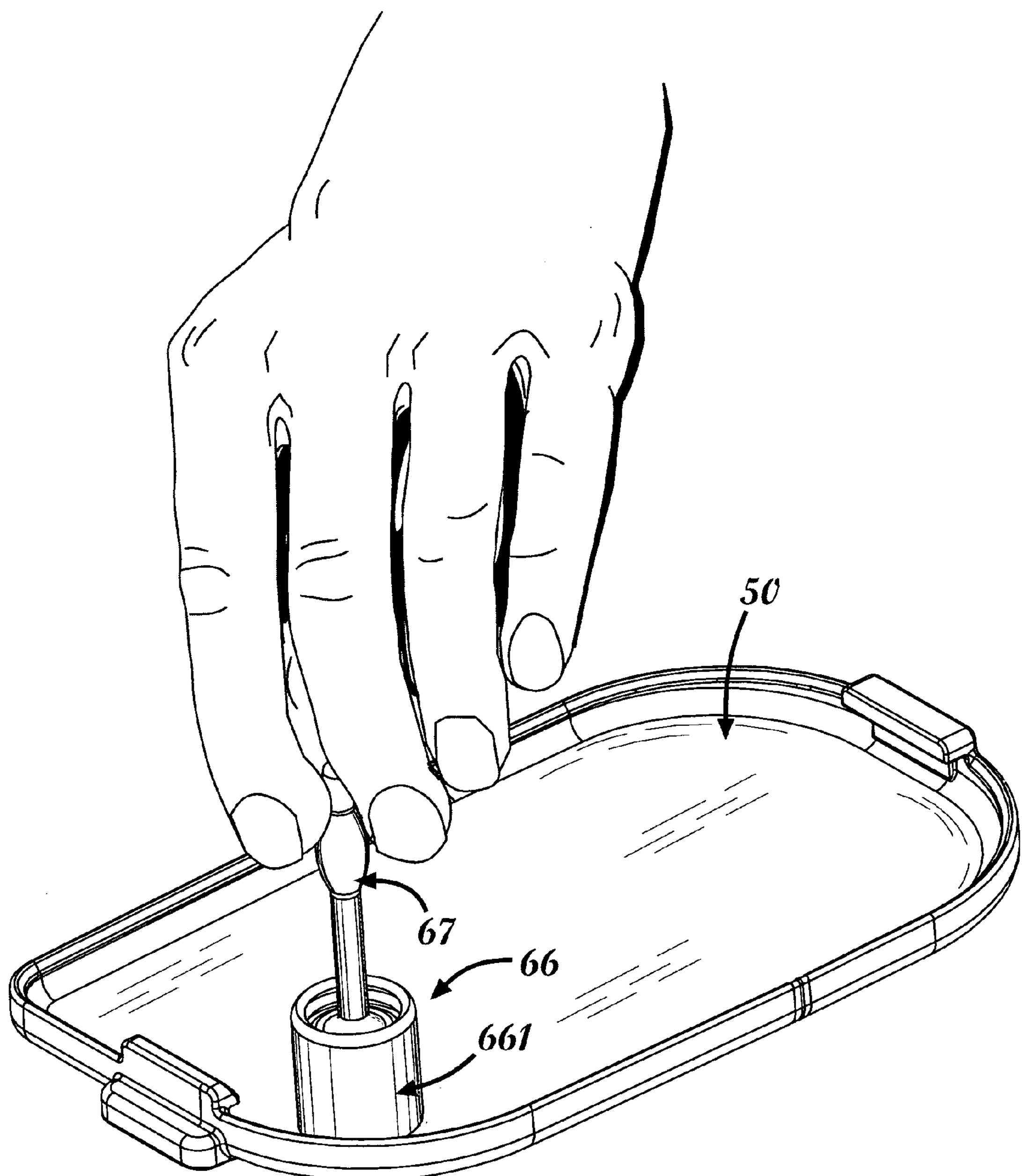
Figure 12A:
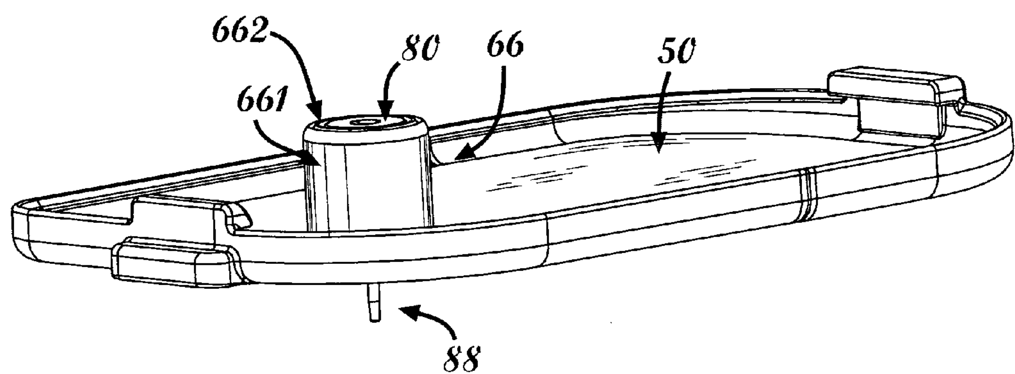
FIGS. 12*a*-12*c* show the well in FIGS. 11*a*-11*b* at a maximum functional height (FIGS. 12*a*, 12*c*) and at a minimum functional height (FIG. 12*b*, 12*c*) according to some embodiments of the disclosure.
Figure 12B:
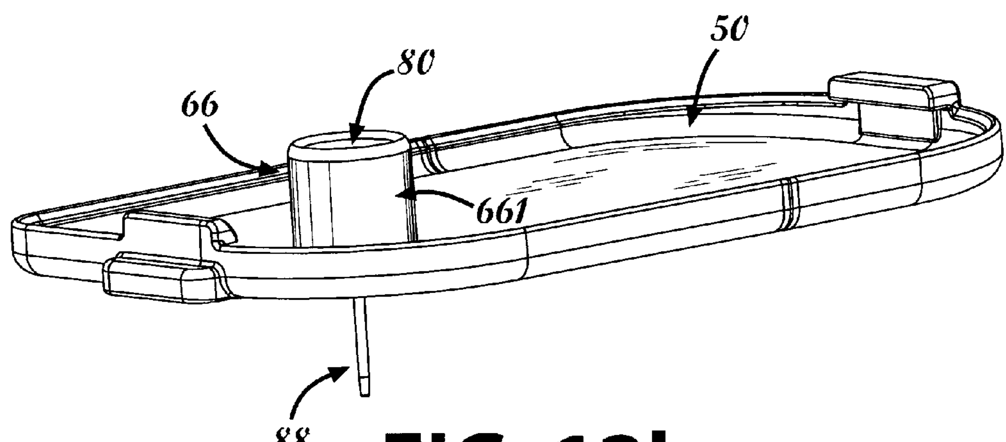
Figure 12C:
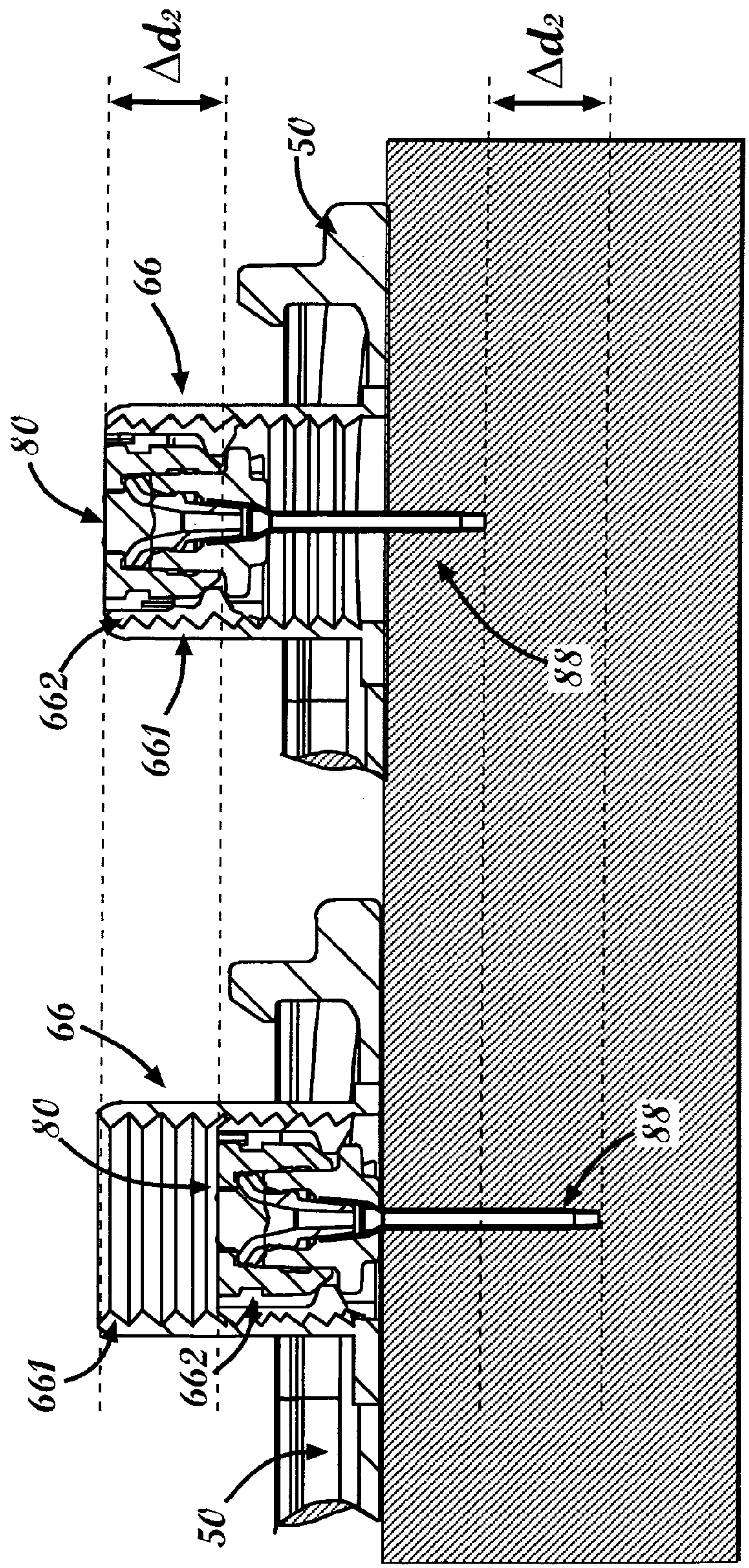

FIGS. 11*a*-11*b* show a patient using rod 67 to rotate displaceable part 662 (not shown in FIGS. 11*a*-11*b*) within stationary part 661. FIG. 12*a* shows well 66 at a maximum functional height. The upper edge of the stationary part 661 of the well 66 may include one or more projections or stops (not shown) that prevent displaceable part 662 from moving linearly beyond the upper edge of the stationary part 661. FIG. 12*b* shows the well 66 after the displaceable part 662 (not shown in FIG. 12*b*) has been rotated within the stationary part 661 to adjust the functional height of the well 66 to a height less than that depicted in FIG. 12*a* (e.g., to a minimum functional height). FIG. 12*c* shows a side-by-side comparison of the well 66 at a maximum functional height (on the right) and the well 66 at a minimum functional height (on the left), after insertion of the cannula 88 into the body. In some embodiments, the functional height (maximum, minimum or otherwise) of the well may be adjusted and set before insertion of the cannula 88 into the body. The change in positioning of the displaceable part 662 within the stationary part 661 (e.g., from maximum height to minimum height, as shown in FIGS. 12*a* and 12*b*) results in changes in insertion depth of the cannula 88 within the body. The change or difference in insertion depth (which corresponds to the "travel" distance of the displaceable part 662 within the stationary part 661) is marked in FIG. 12*c* as "$\Delta d_2$".

Figure 13B:
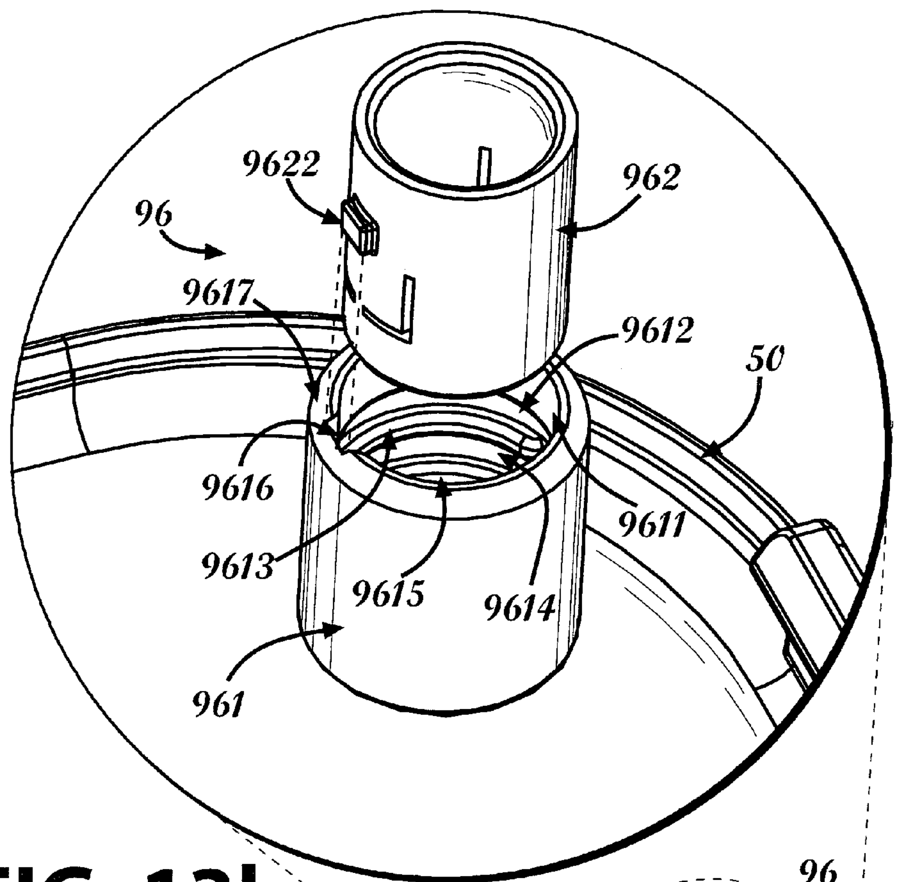
FIGS. 13*a*-14*b* show an embodiment of an adjustable mounting assembly in which only the functional height of a well of the cradle unit is adjustable according to some embodiments of the disclosure.
Figure 13A:
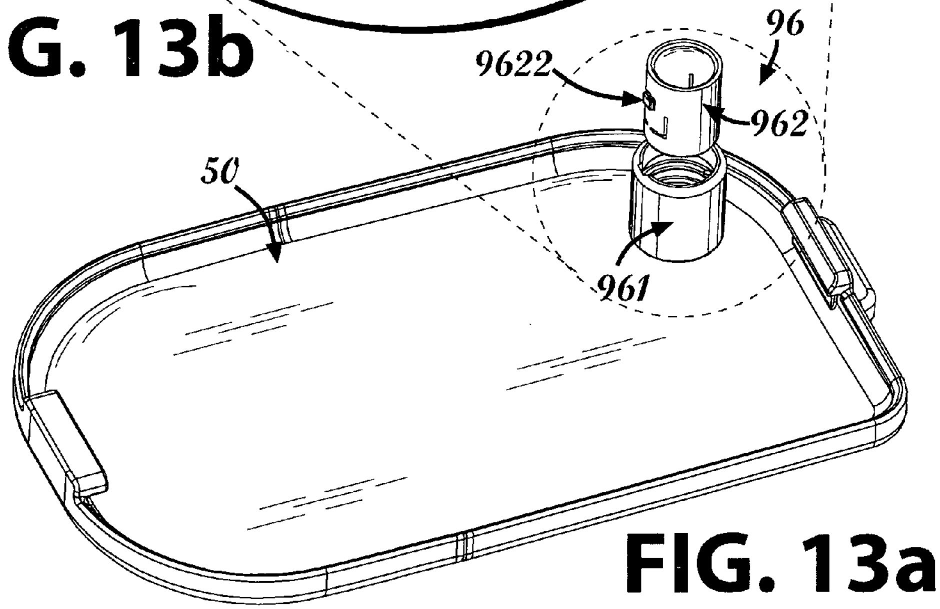

FIGS. 13*a*-13*b* show an embodiment of a two-part well 96 having a height adjusting mechanism using grooves and matching protrusions. The two-part well 96 may include a stationary part 961 and a displaceable part 962. In some embodiments, displaceable part 962 may have anchoring mechanisms (not shown) for engaging and maintaining a cannula unit (e.g., cannula unit 80). In some embodiments, the internal surface of the stationary part 961 may include a plurality of grooves (e.g., two grooves 9612 and 9614) and the external surface of displaceable part 962 may have one or more protrusions 9622 dimensioned to fit within the grooves 9612 and 9614. In some embodiments, groove 9612 may be defined by an upper rim 9611 and an inner rim 9613 and groove 9614 may be defined by inner rims 9613 and 9615, as shown in FIG. 13*b*. In some embodiments, stationary part 961 may include one or more substantially vertical channels having a width substantially matching the width of protrusion 9622 to allow protrusion 9622 to slide therein and thus provide for vertical displacement of displaceable part 962 within stationary part 961.

For example, stationary part 961 may include a channel 9616 extending from an upper edge 9617 of the stationary part 961, through groove 9612, and down to inner rim 9613. In some embodiments, the displaceable part 962 can only be coupled to the stationary part 961 when the protrusion 9622 is aligned with the channel 9616, as shown in FIG. 13*b*. Once the protrusion 9622 reaches the end of the channel 9616 (i.e., it encounters inner rim 1613) the displaceable part 962 can no longer be displaced downwardly and can only be rotated within stationary part 961 by sliding protrusion 9622 within the groove 9612. In some embodiments, prior to coupling a cannula unit (not shown) to the well 96, a patient may rotate the displaceable part 962 through groove 9612, such that protrusion 9622 is positioned between upper rim 9611 and inner rim 9613 and displaceable part 962 cannot be displaced vertically. In some embodiments, a patient may use a tool (not shown) for displacing displaceable part 962 within stationary part 961. The tool (e.g., a rod) may be coupled to displaceable part 962 by engaging with the anchoring mechanisms within displaceable part 962, or by one or more protrusions on the tool engaging with one or more recesses within displaceable part 962 (not shown in FIGS. 13*a*-13*b*) or in any other suitable way.

Figure 13C:
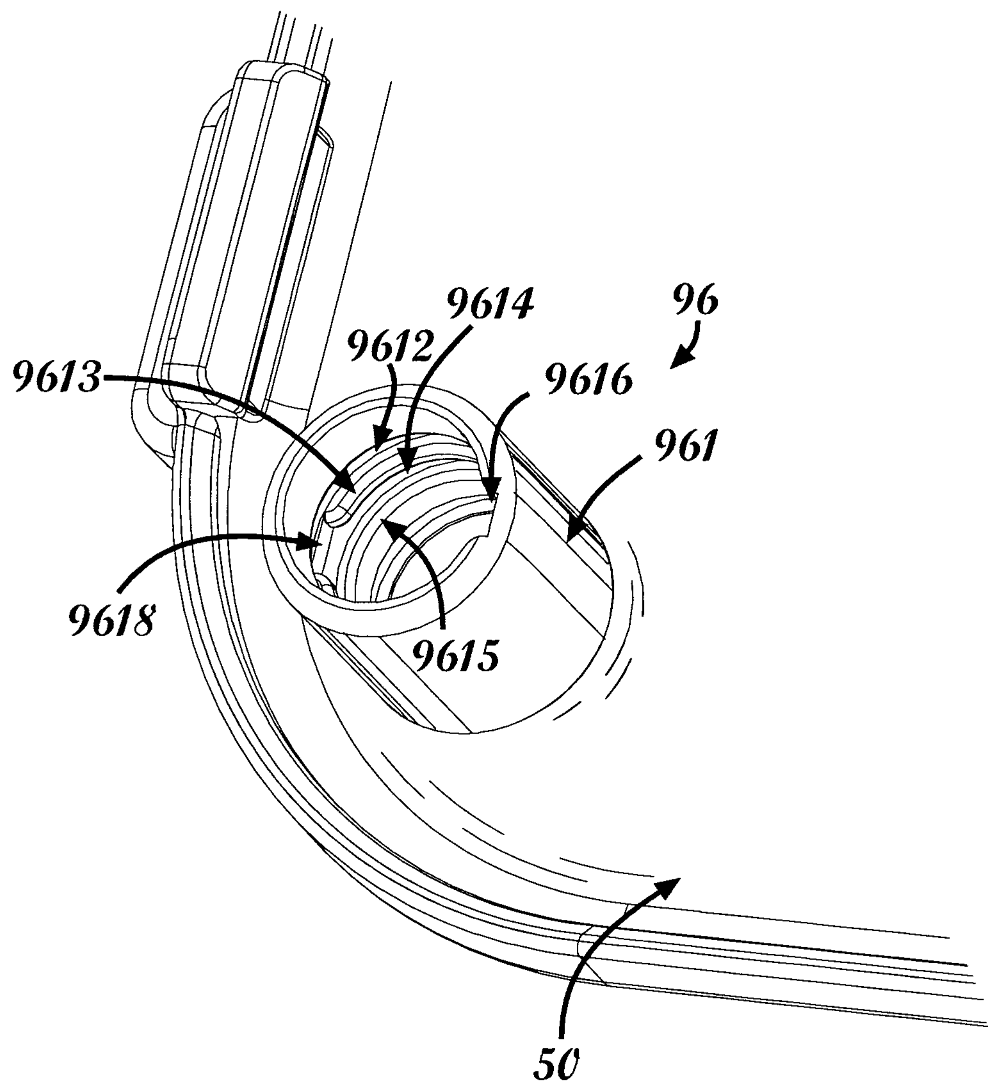

As shown in FIG. 13*c*, in some embodiments the stationary part 961 may include another substantially vertical channel 9618 with width substantially matching the width of the protrusion 9622 to allow further vertical displacement of the displaceable part 962 within the stationary part 961. For example, channel 9618 may extend from groove 9612 to groove 9614, through inner rim 9613. Channel 9618 may be located directly beneath channel 9616, thus forming together a single longer channel, or it may be located anywhere else along the interior of stationary part 961 (e.g., opposite channel 9616), as shown in FIG. 13*c*. A user may thus further lower the functional height of the well 96 and, in some embodiments, also the absolute height of the well 96, by rotating displaceable part 962 within stationary part 961 until protrusion 9622 is aligned with channel 9618 and then displacing displaceable part 962 further downwardly within the stationary part 961 by sliding protrusion 9622 within channel 9618. Once the protrusion 9622 reaches the end of the channel 9618 (i.e., it encounters the inner rim 9615), the displaceable part 962 can no longer be displaced downwardly and can only be rotated within the stationary part 961 by sliding protrusion 9622 within groove 9614. The user may then rotate displaceable part 962 within stationary part 961 through groove 9614, such that protrusion 9622 is positioned between inner rim 9613 and inner rim 9615 and displaceable part 962 cannot be displaced vertically.

Figure 14A:
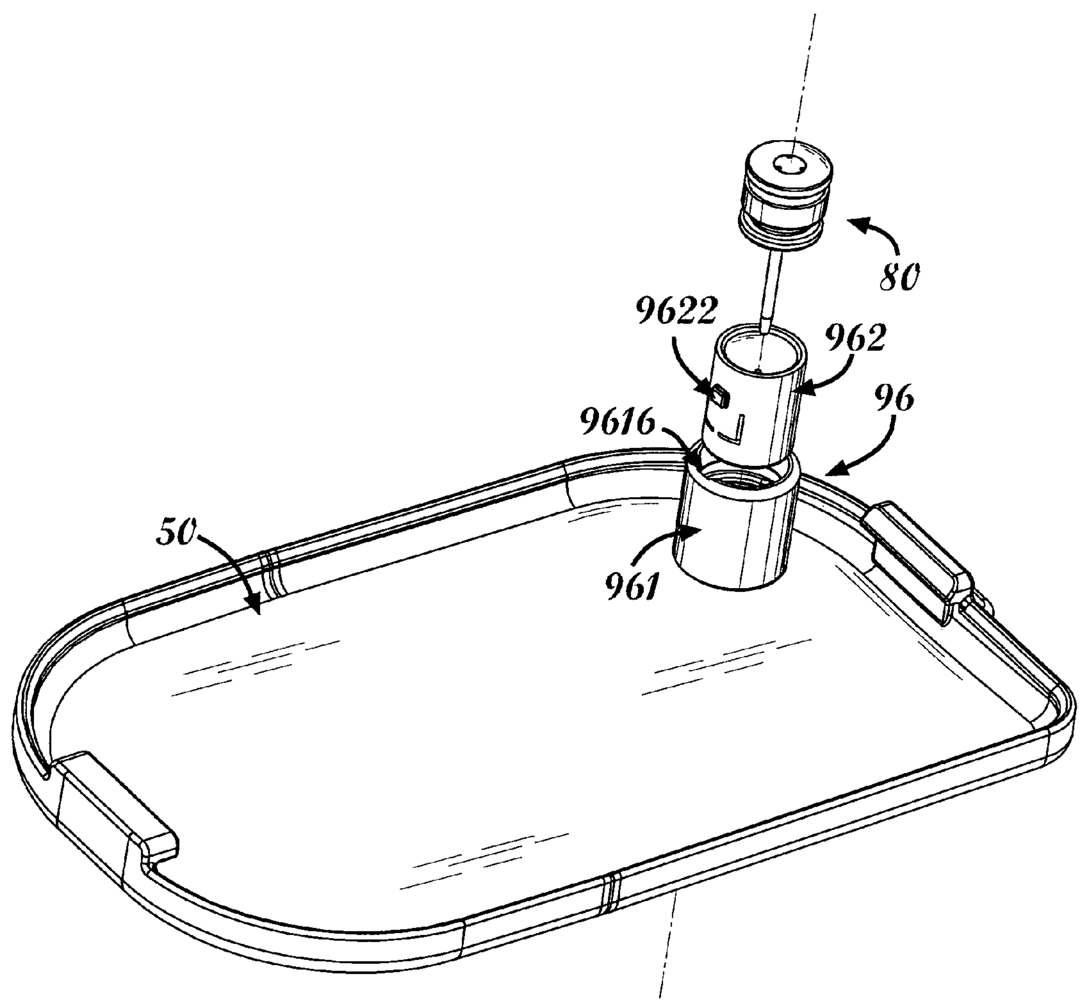
Figure 14B:
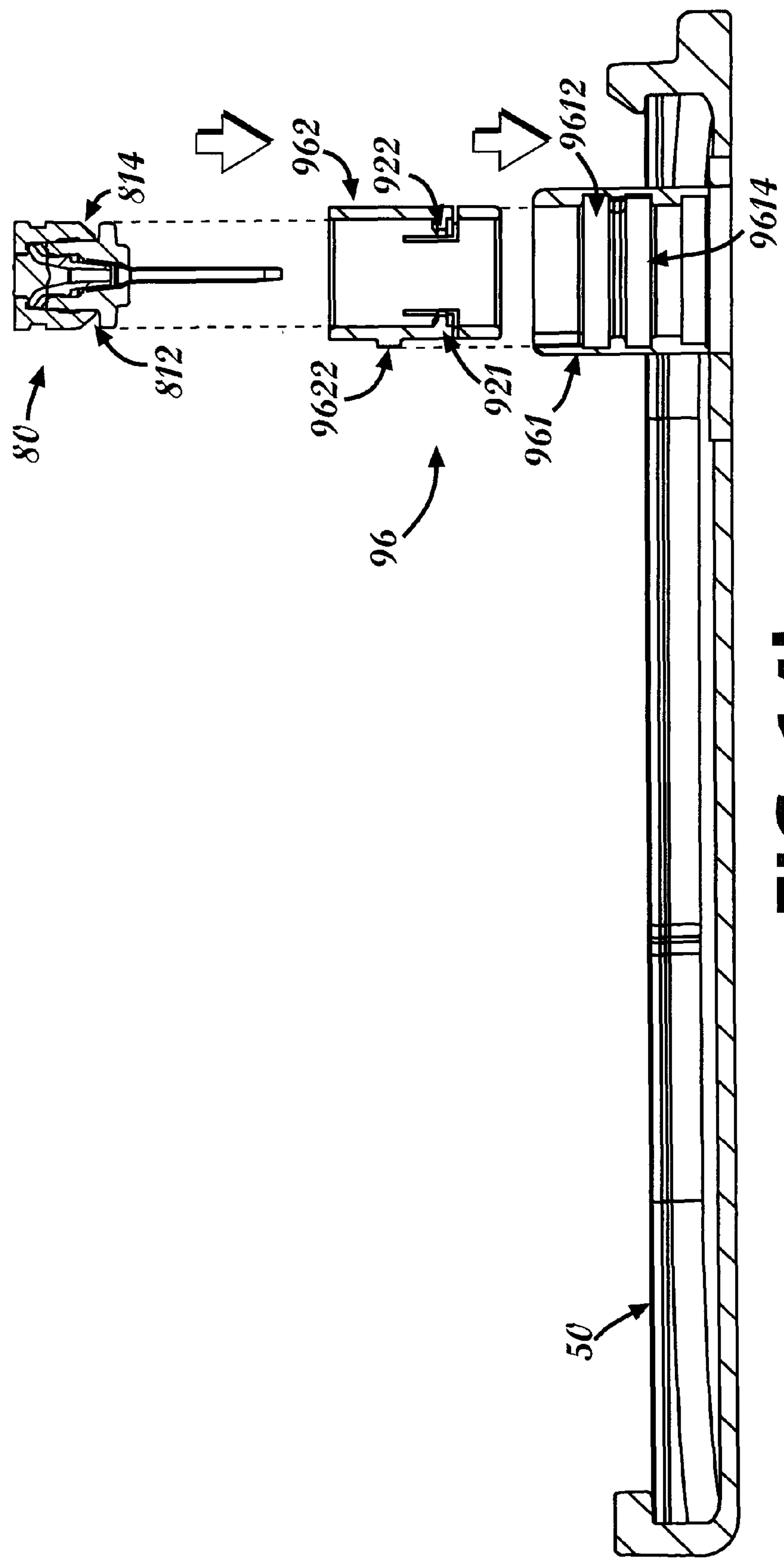

FIGS. 14*a*-14*b* show an embodiment of the two-part well 96, along with cradle 50 and a cannula unit 80 prior to coupling displaceable part 962 to stationary part 961 and prior to inserting cannula unit 80 within the well 96. Upon inserting cannula unit 80 within the well 96, anchoring mechanisms (e.g., latches) 921, 922 located on the interior of the displaceable part 962 (shown in FIG. 14*b*) may be received within one or more recesses 812, 814 (or within a single annular recess) on cannula unit 80 to establish a secure connection of cannula unit 80 with cradle 50.

Figure 15:
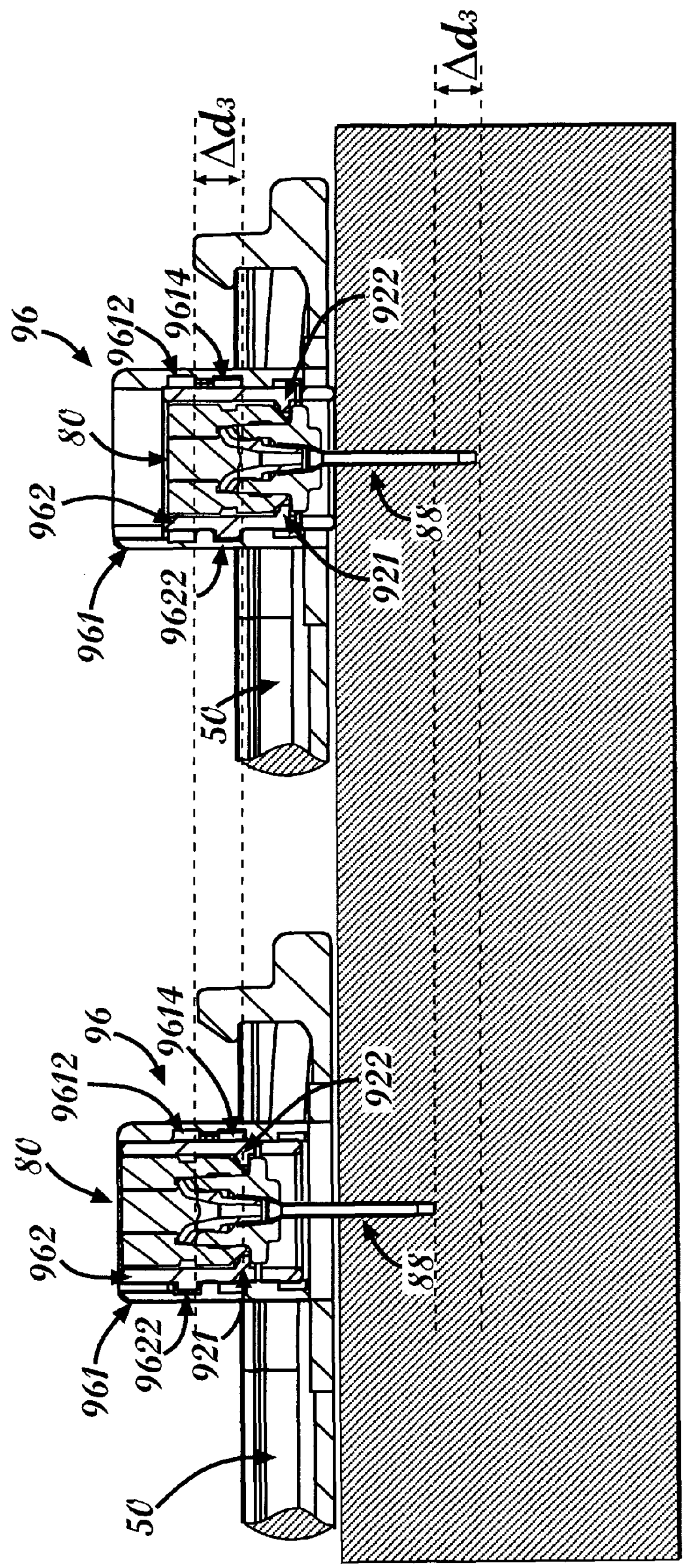
FIG. 15 shows a cross-sectional view of the well in FIGS. 13*a*-14*b* at a maximum functional height and at a minimum functional height according to some embodiments of the disclosure.

FIG. 15 shows a side-by-side comparison of the well 96 at a maximum functional height (on the left), for example, when protrusion 9622 is positioned within groove 9612, and the well 96 at a minimum functional height (on the right), for example, when protrusion 9622 is positioned within groove 9614, after insertion of the cannula 88 into the body through the well 96. In some embodiments, the functional height (maximum, minimum or otherwise) of the well 96 may be adjusted and set before insertion of the cannula 88 into the body. The change in positioning of the displaceable part 962 within the stationary part 961 (e.g., from maximum height to minimum height) results in a change in insertion depth of the cannula 88 within the body. This change or difference in insertion depth (which corresponds to the distance between the upper groove 9612 and the lower groove 9614), is marked in FIG. 15 as "$\Delta d_3$".

Some embodiments of the present disclosure may be directed to a well having one or more sets of anchoring mechanisms (e.g., latches) positioned at different locations along the vertical length of the well (i.e., at different heights relative to the mounting base). In some embodiments, the well may be configured such that only one set of anchoring mechanisms function at a time (i.e., only one set can capture and secure the cannula unit within the well). Therefore, in some embodiments, the functional height of the well is determined by whichever set of anchoring mechanisms is the functional set. In some embodiments, choosing which set of anchoring mechanisms will be functional may also dictate the absolute height of the well. It should be noted that in case a single anchoring mechanism is sufficient to anchor the cannula unit 80 within the well 96 (e.g., an annular or a semi-annular latch), as opposed to a set of anchoring mechanisms, the height adjusting mechanism embodiments described with respect to FIGS. 16*a*-18*b* would require a minimum of two anchoring mechanisms located at different heights along the well.

Figure 16A:
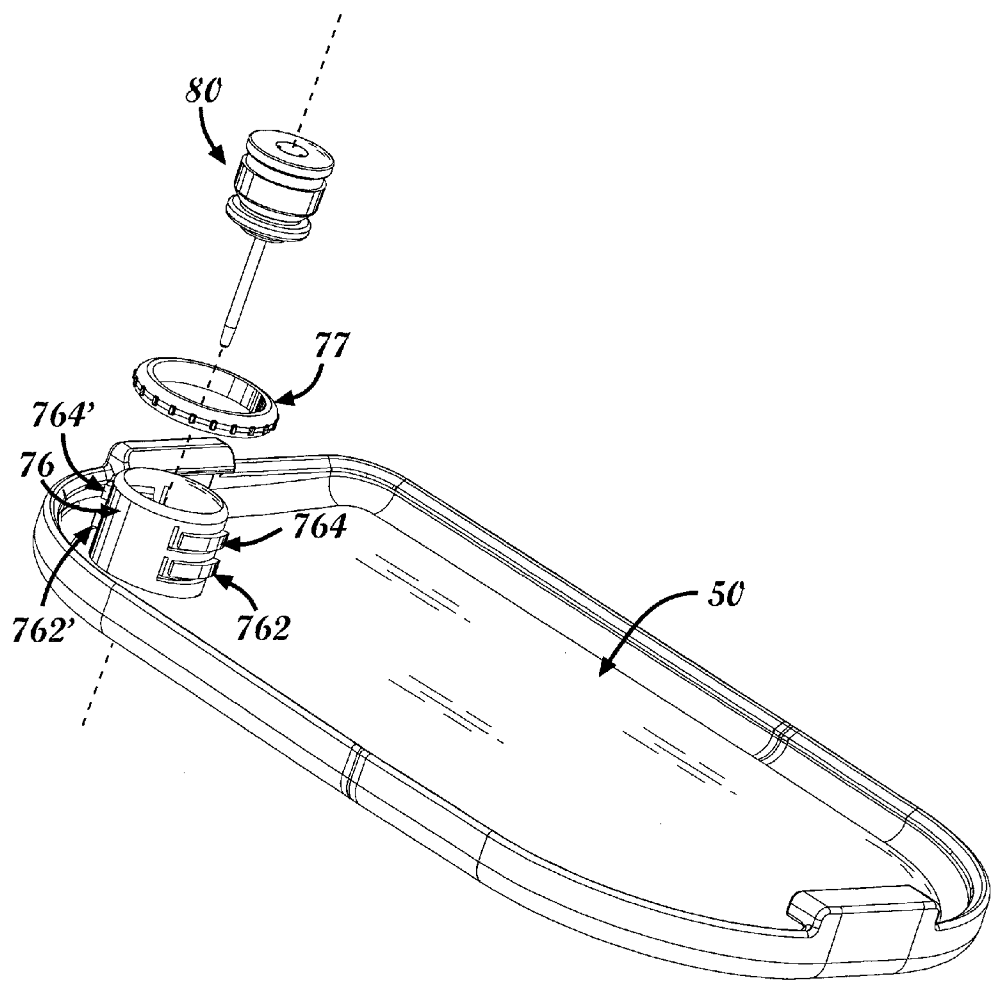
FIGS. 16*a*-16*b* show an embodiment of an adjustable mounting assembly in which a well of the cradle unit contains multiple anchoring mechanisms for adjusting the functional height of the well according to some embodiments of the disclosure.
Figure 16B:
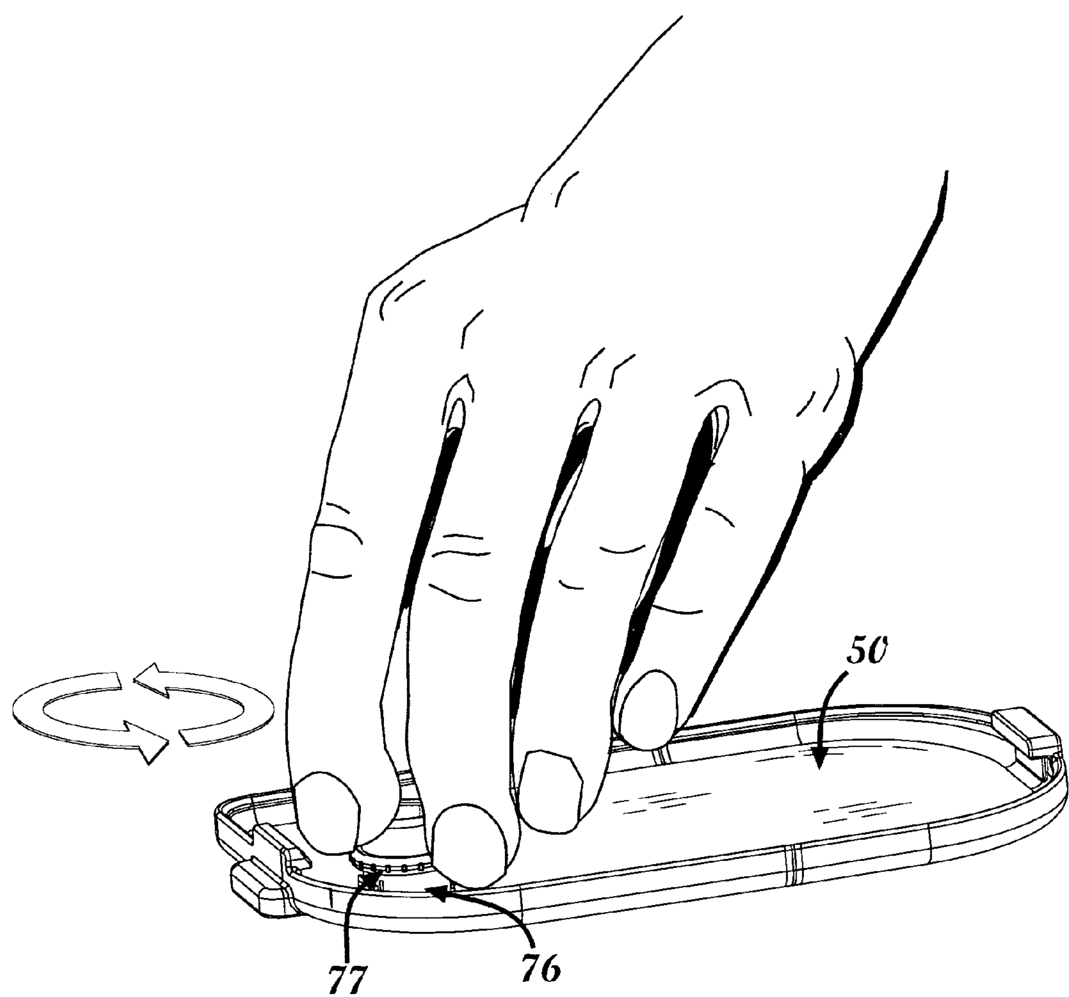

FIGS. 16*a*-18*b* show an embodiment of a one-piece well 76 having a height adjusting mechanism employing two sets of anchoring mechanisms (e.g., latches) within the well. As shown in FIG. 16*a*, the well 76 may include, for example, a first set of anchoring mechanisms 764, 764' and a second set of anchoring mechanism 762, 762'. In some embodiments, setting one set of anchoring mechanisms (e.g., latches) to be functional may be carried out using one or more retaining components 77. In some embodiments, the anchoring mechanisms may be flexible, at least in part, and setting one set of anchoring mechanisms to be functional may be carried out by positioning the retaining component 77 over that set of anchoring mechanisms such that it prevents the anchoring mechanisms of the chosen set from bending outwardly. In some embodiments, the retaining component 77 is configured to push one set of latches inwardly to render it functional. The retaining component 77 may be annular (e.g., configured as a retaining ring surrounding the well 76). FIG. 16*b* shows a patient using the retaining component 77 to set one set of anchoring mechanisms to be functional, for example, by rotating the retaining component 77 onto and overtop of the chosen anchoring mechanisms. In some embodiments, the retaining component 77 is displaced up and down the well 76 by being pushed and pulled along the well exterior.

Figure 17A:
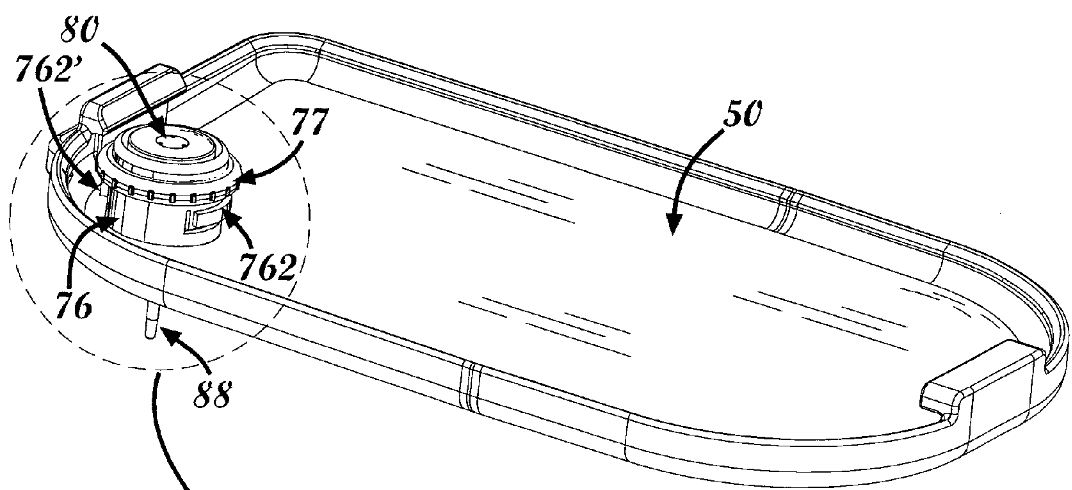
FIGS. 17*a*-17*b* show the well in FIGS. 16*a*-16*b* after setting a first anchoring mechanism in a functional mode and connecting a cannula unit to the well according to some embodiments of the disclosure.
Figure 17B:
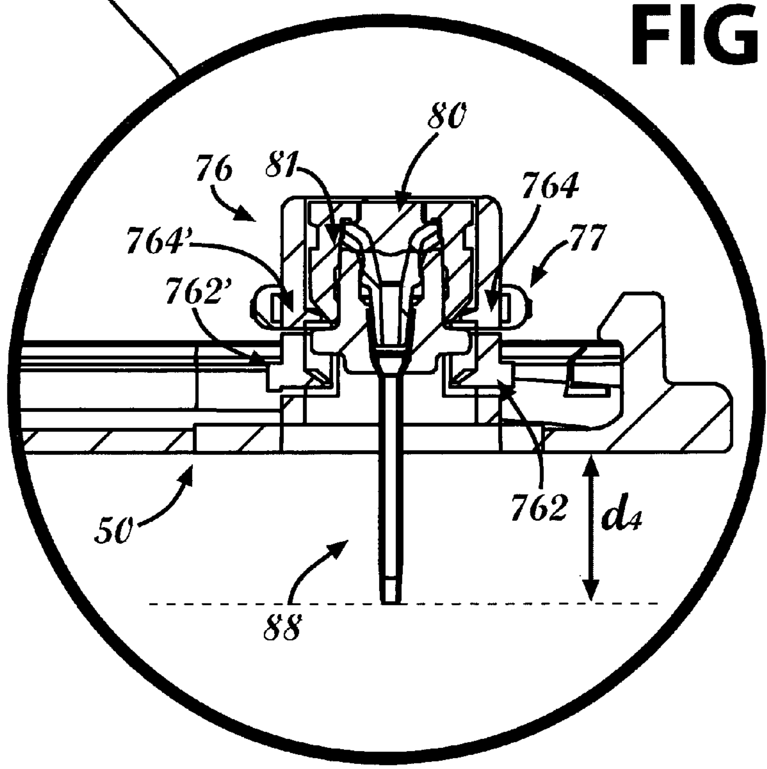

FIG. 17*a* shows the well 76 after setting anchoring mechanisms 764, 764' as the functional set, and after coupling the cannula unit 80 to the well 76. As shown in FIG. 17*b*, the retaining component 77 may be positioned to prevent anchoring mechanisms 764, 764' from bending outwardly as the cannula unit 80 is being inserted (e.g., using an inserter) into the well 76. Thus, as the cannula unit 80 is inserted into the well 76, it does not reach anchoring mechanisms 762, 762', as the cannula hub 81 is captured by the anchoring mechanisms 764, 764' to provide for a cannula insertion depth $d_4$, as shown in FIG. 17*b*.

Figure 18A:
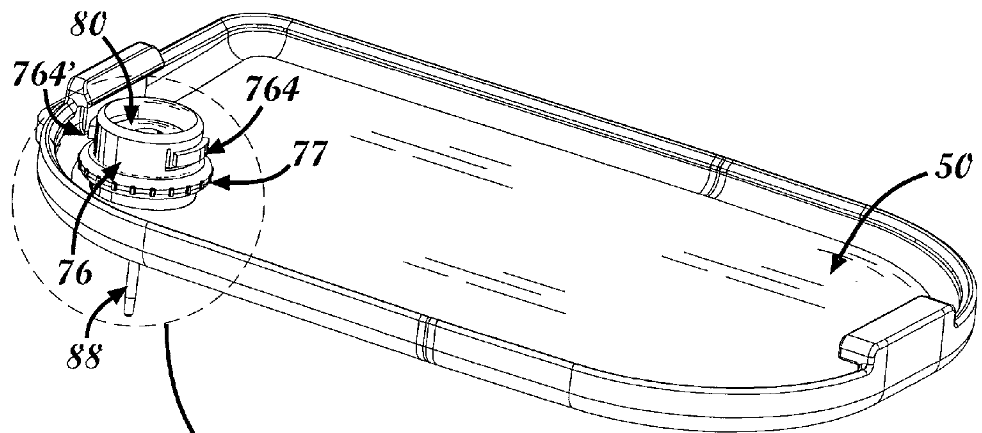
FIGS. 18*a*-18*b* show the well in FIGS. 16*a*-16*b* after setting a second anchoring mechanism in a functional mode and connecting a cannula unit to the well according to some embodiments of the disclosure.
Figure 18B:
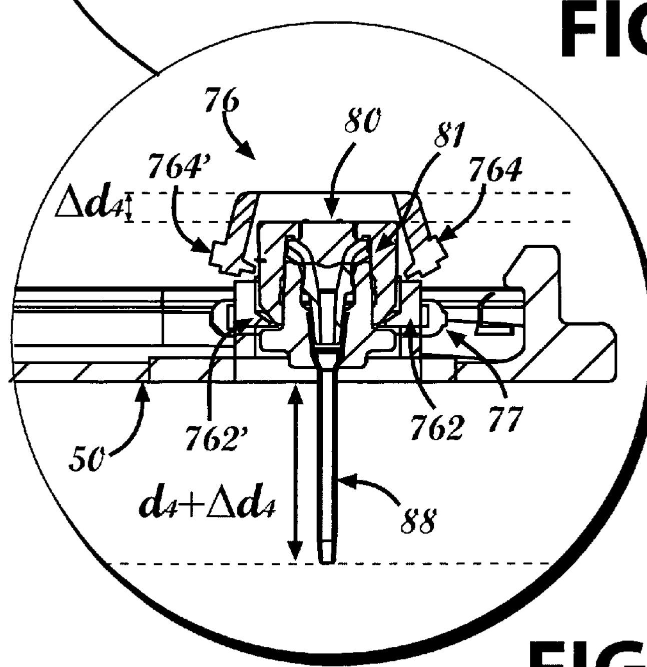

FIG. 18*a* shows the well 76 after setting anchoring mechanisms 762, 762' as the functional set and after coupling the cannula unit 80 to the well 76. As shown in FIG. 18*b*, the retaining component 77 may be positioned to prevent anchoring mechanisms 762, 762' from bending outwardly as cannula unit 80 is being inserted (e.g., using an inserter) into the well 76. Therefore, as the cannula unit 80 is inserted into the well 76, it pushes anchoring mechanisms 764, 764' outwardly during contact and continues advancing downwardly toward anchoring mechanisms 762, 762', where the cannula hub 81 is captured by anchoring mechanisms 762, 762', which are held inwardly by retaining component 77. As the cannula hub 81 is now engaged at the lower anchoring mechanisms 762, 762', the cannula insertion depth is now $d_4+\Delta d_4$, where $\Delta d_4$ is the additional "travel" distance of the cannula unit 80 within the well 76, which equals the vertical distance between the upper set of anchoring mechanisms 764, 764' and the lower set of anchoring mechanisms 762, 762'.

In some embodiments, setting one set of anchoring mechanisms as the functional set may be carried out by pivotally displacing the anchoring mechanisms. In some embodiments, the well may be provided with at least one hinged portion to enable such displacing. For example, where two sets of anchoring mechanisms are employed, the well may include two panels (e.g., substantially vertical panels) configured to pivot about an axis. Each panel may include one anchoring mechanism from each of the two sets (i.e., each panel may include two anchoring mechanisms located one above the other, one above the axis and one below the axis). The upper set of anchoring mechanisms may thus be set as the functional set of anchoring mechanisms by causing both panels to pivot such that the upper portion of each panel (i.e., the portion above the axis) is pushed inwardly into the well, and the lower portion of each panel (i.e., the portion below the axis) is pushed outwardly from the well. A retaining component, e.g., a retaining component similar to that depicted in FIGS. 16*a*-18*b*, may be used to maintain the slanted positioning of the panels. Similarly, the lower set of anchoring mechanisms may be set as the functional set of anchoring mechanisms by causing both panels to pivot such that lower portion of each panel is pushed inwardly within the well, and the upper portion of each panel is pushed outwardly from the well.

Figure 19:
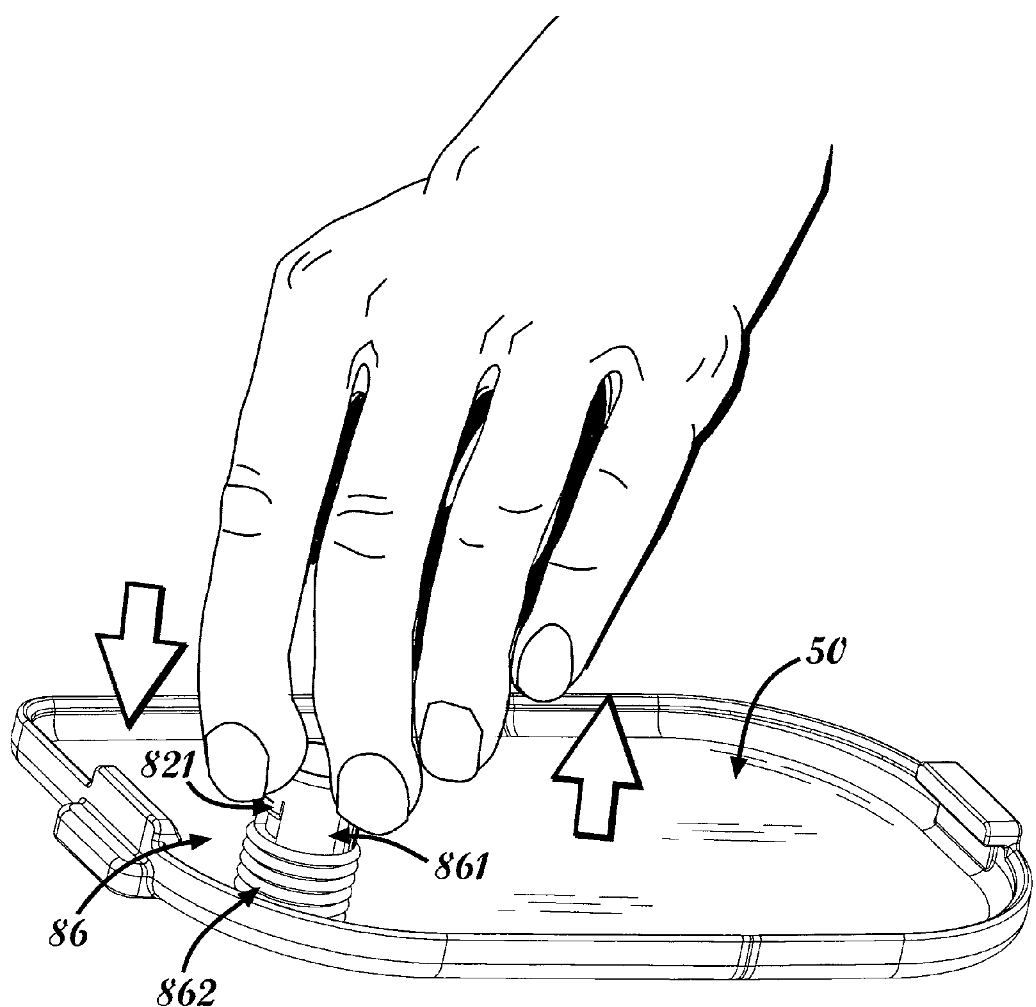
FIG. 19 shows an embodiment of an adjustable mounting assembly having an accordion-type height adjusting mechanism, according to some embodiments of the disclosure.

FIG. 19 shows an embodiment of a well 86 having an accordion-type height adjusting mechanism according to the present disclosure. In some embodiments, at least a portion of the well 86 may be configured with one or more folds akin to the bellows of an accordion. For example, the well 86 may comprise at least one rigid portion 861 (e.g., made from plastic) having anchoring mechanisms (only one anchoring mechanism, 821, is shown in FIG. 19) and at least one accordion-shaped portion 862 (or "accordion portion") located below the anchoring mechanisms. That is, the well 86 is a single integral part with a portion of its structure being configured as an accordion. Thus, a patient can adjust the functional and/or absolute height of the well 86 by pushing the well 86 downwardly to compress the accordion portion 862 or pulling the well 86 upwardly to stretch the accordion portion 862. In some embodiments, the anchoring mechanisms may be included in the accordion-shaped portion 862.

Figure 20A:
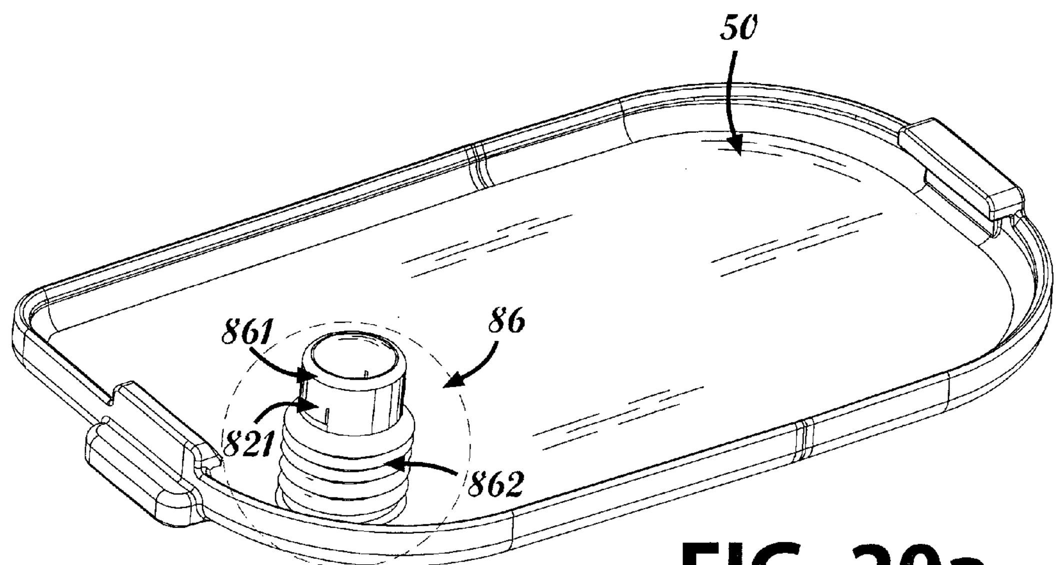
FIGS. 20*a*-20*b* show the well in FIG. 19 after extending the accordion-type height adjusting mechanism and connecting a cannula unit to the well according to some embodiments of the disclosure.
Figure 20B:
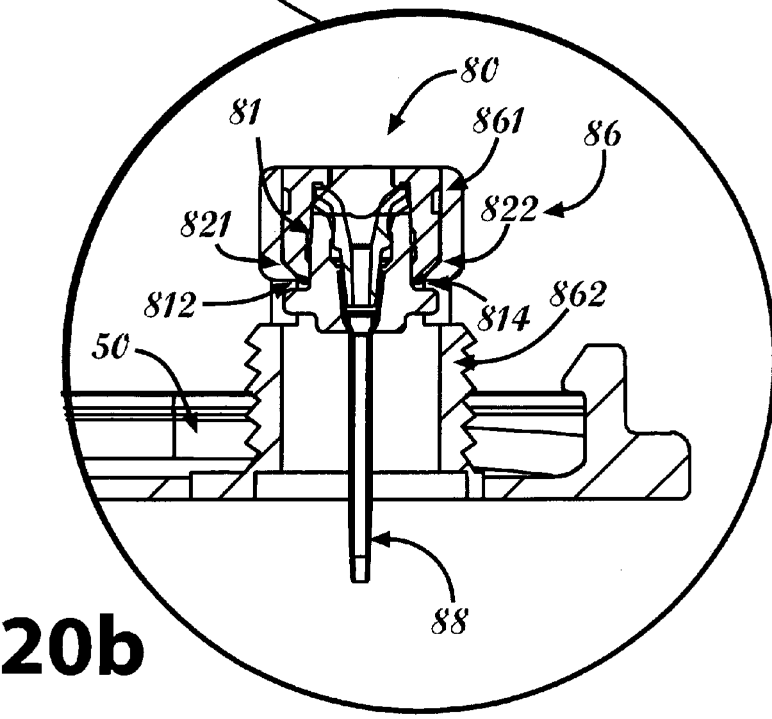

FIG. 20*a* shows the well 86 after pulling it up such that the accordion portion 862 is, for example, at its maximum stretched state. As shown in FIG. 20*b*, after inserting the cannula unit 80 within the well 86, the anchoring mechanisms 821, 822 are captured by corresponding recesses 812, 814 of cannula hub 81 to secure the cannula unit 80 within the well 86.

Figure 21B:
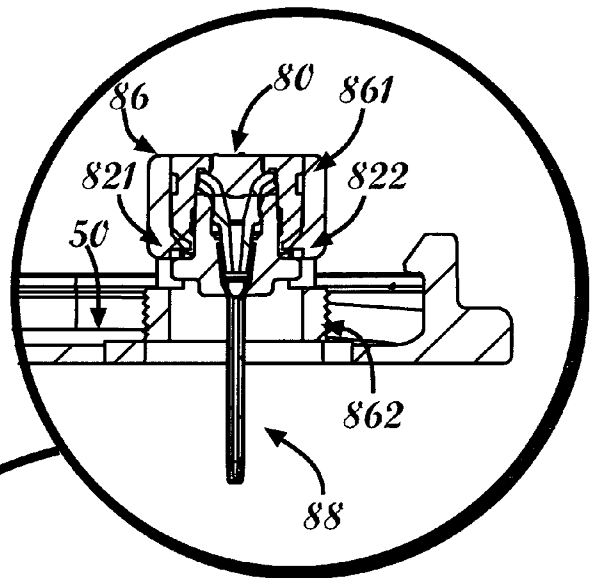
FIGS. 21*a*-21*b* show the well in FIG. 19 after compressing the accordion-type height adjusting mechanism and connecting a cannula unit to the well according to some embodiments of the disclosure.
Figure 21A:
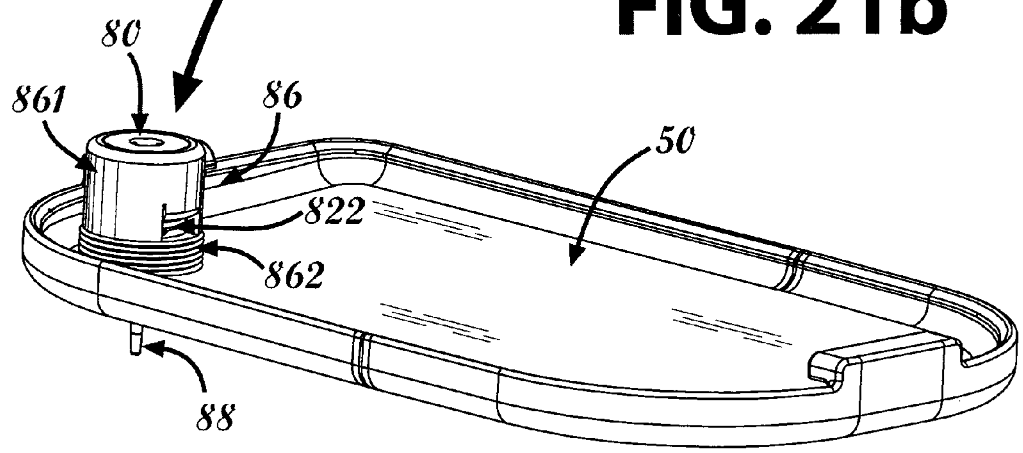

FIG. 21*a* shows the well 86 after pushing it down such that the accordion portion 862 is, for example, at its maximum compressed state and after coupling the cannula unit 80 to the well 86. As shown in FIG. 21*b*, the cannula unit 80 is secured within the well 86 using anchoring mechanisms 821, 822, which may be part of the rigid portion 861 of the well 86. The change or difference in cannula insertion depth corresponds to the difference in length of the accordion portion 862 between its stretched state, as shown in FIGS. 20*a*-20*b*, and its compressed state, as shown in FIGS. 21*a*-21*b*.

In some embodiments, the mounting unit (e.g., cradle 50) may include a well that is slanted at an oblique angle relative to the mounting base of the mounting unit so as to define an angled passageway for receiving a cannula unit and inserting a cannula into the body at such an oblique angle. Such a configuration is disclosed, for example, in U.S. Patent Application Publication No. 2008/0215035 to Yodfat et al. and International Publication No. WO 2009/016638 to Yodfat et al., the contents of which are incorporated herein by reference in their entirety. In some embodiments, the mounting unit may include a tiltable well to define a slanted passageway with an adjustable angle, as disclosed, for example, in International Publication No. WO 2009/016638 to Yodfat et al., the content of which is incorporated herein by reference in its entirety. All the height adjusting mechanisms disclosed above may also be implemented in slanted and/or tiltable wells.

According to embodiments of the present disclosure, once the mounting unit is adhered to the skin and the cannula is inserted into the body through the well, a therapeutic device, such as a fluid delivery device and/or an analyte sensing device, may be coupled to the cannula. For example, a fluid delivery device (e.g., an infusion device) may be secured to a skin-adherable cradle, such that upon connection of the device to the cradle, the device's outlet port is fitted onto the cradle's well and a connecting lumen provided at the outlet port pierces the cannula's septum thus enabling fluid communication between the delivery device and the cannula. In some embodiments where the absolute height of the well is fixed, and only the functional height is adjustable, the connecting lumen may be configured to be long enough to pierce the cannula's septum upon connection of the device to the cradle even if the well is set to its minimum functional height. In some embodiments where the absolute height of the well is also adjustable, the outlet port may be configured to be deep enough so that the outlet port is able to fit over the well upon connection of the device to the cradle even if the well is set to its maximum absolute height, and the connecting lumen may be configured to be long enough to pierce the cannula's septum upon connection of the device to the cradle even if the well is set to its minimum absolute (and functional) height. According to some embodiments, a manufacturer and/or distributer of a fluid delivery device may provide a user/patient with several devices, or with several disposable parts in the case of a two-part device having reusable and disposable parts, which have varying outlet port depths and/or varying connecting lumen lengths, so that the patient can adjust the absolute and/or functional height of the well according to the desired cannula insertion depth, and then use the delivery device (or the disposable part) having the outlet port depth and/or the connecting lumen length suitable for use with the set absolute and/or functional height of the well.

Figure 22A:
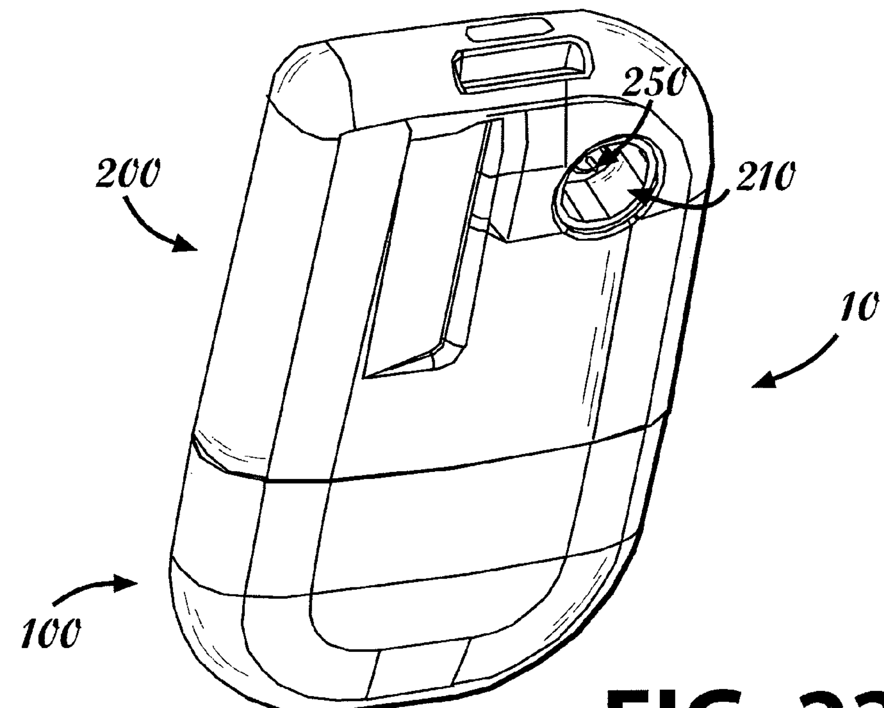
FIGS. 22*a*-22*b* show two therapeutic devices having connecting lumens with substantially the same length and outlet ports with different depths according to some embodiments of the disclosure.
Figure 22B:
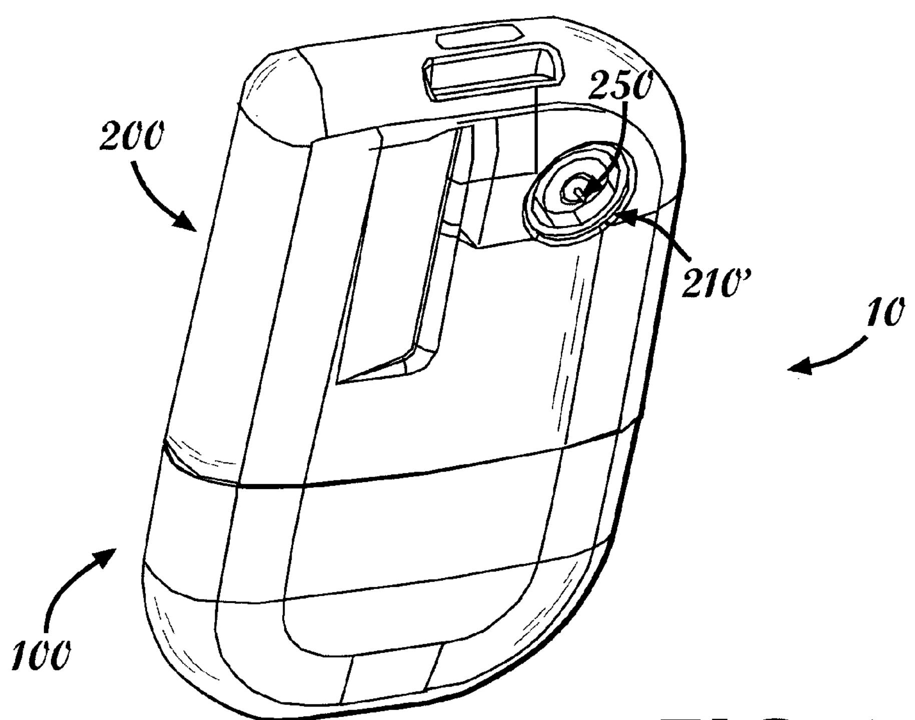

FIGS. 22*a*-22*b* show, for example, two therapeutic devices 10, e.g., devices having a reusable part 100 and a disposable part 200, provided with connecting lumens 250 having substantially the same length, however, the outlet port 210 shown in FIG. 22*a* is deeper than the outlet port 210' shown in FIG. 22*b*, to enable connection to a cradle having a well with a greater absolute height.

In some embodiments where the absolute height of the well is adjustable, the depth of the outlet port and the length of the connecting lumen may be uniform and corresponding to the well at its minimum absolute height, and if the absolute height of the well is set to be higher than the minimum absolute height of the well, then prior to connecting a therapeutic device to the cradle, the patient may connect a dedicated platform to the bottom surface of the device and/or to the upper surface of the cradle, thereby effectively elevating the device to properly fit over the well.

In some embodiments, the depth of the outlet port, the length of the connecting lumen and/or the positioning of the connecting lumen within the outlet port may also be adjustable, according to the set functional and/or absolute height of the well.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the disclosure as defined by the exemplary appended claims and equivalents thereto. The contents of any references cited throughout this application are hereby incorporated by reference. The appropriate components, processes, and methods of those documents may be included as support for one or another of the disclosed embodiments.

What is claimed is:

1. A system for adjusting an insertion depth of a cannula associated with a portable therapeutic device, the system comprising:

a mounting unit securable to the skin of a patient and having a mounting base and a well defining a passageway through the mounting base, the well comprising a first part and a second part displaceable relative to the first part; and a cannula unit including a cannula subcutaneously insertable through the well of the mounting unit, wherein the second part of the well and the cannula unit are configured and arranged to define a space therebetween for receiving an adjustment tool in the space to adjust an insertion depth of the cannula within the body of the patient.

2. The system according to claim 1, wherein the cannula unit is coupleable to the mounting unit.

3. The system according to claim 1, wherein the second part comprises one or more anchoring mechanisms for coupling to the cannula unit.

4. The system according to claim 3, wherein displacing the second part relative to the first part alters the height of the well and displaces the one or more anchoring mechanisms.

5. The system according to claim 3, wherein the well has a fixed height and displacing the second part relative to the first part displaces the one or more anchoring mechanisms within the well.

6. The system according to claim 3, wherein the first part and the second part are substantially concentric and the second part is displaceable within the first part.

7. The system according to claim 6, wherein:

the first part comprises a plurality of threads disposed along at least a portion of the interior of the first part; and the second part comprises a plurality of threads disposed along at least a portion of the exterior of the second part, wherein the plurality of threads of the first part are configured to interact with the plurality of threads of the second part to displace the second part relative to the first part.

8. The system according to claim 6, wherein:

the first part is configured with at least one groove disposed along the interior of the first part; and the second part is configured with at least one protrusion disposed along the exterior of the second part, wherein the at least one protrusion of the second part is configured to be received within the at least one groove of the first part to displace the second part relative to the first part.

9. The system according to claim 3, wherein the first part and the second part are substantially concentric and the second part is displaceable externally to the first part.

10. The system according to claim 3, wherein the second part is configured for threaded engagement with the first part.

11. The system according to claim 3, wherein the system further comprises the adjustment tool, the tool being configured to be coupled to the second part and displace the second part relative to the first part.

12. The system according to claim 1, wherein the well further comprises at least one anchoring mechanism to enable coupling of the cannula unit to the mounting unit.

13. The system according to claim 12, wherein the system further comprises a retaining component that is configured to be positioned over the least one anchoring mechanism to at least one of push the at least one anchoring mechanism inwardly and prevent the at least one anchoring mechanism from being pushed outwardly from the well, to enable the coupling of the cannula unit to the mounting unit.

14. The system according to claim 13, wherein the at least one anchoring mechanism comprises a plurality of sets of anchoring mechanisms, wherein:

each set of the plurality of sets of anchoring mechanisms includes one or more anchoring mechanisms; and the retaining component is configured to be positioned over one set of anchoring mechanisms at a time.

15. The system according to claim 1, wherein at least a portion of the well is configured with one or more folds akin to the bellows of an accordion.

16. The system according to claim 1, wherein the mounting base further comprises an adhesive tape to secure the mounting unit to the skin of the patient.

17. The system according to claim 1, wherein the well is provided at an oblique angle with respect to a contact surface of the mounting base that contacts the skin of the patient when the mounting base is secured to the skin of the patient, to enable insertion of the cannula at an oblique angle with respect to the skin of the patient.

18. The system according to claim 1, wherein the angle of the well relative to a contact surface of the mounting base that contacts the skin of the patient when the mounting base is secured to the skin of the patient is adjustable to enable insertion of the cannula at varying angles.

19. The system according to claim 1, wherein the cannula is adapted to sense a bodily analyte.

20. The system according to claim 1, wherein the system is configured to enable adjustment of the well after connection of the cannula unit.

21. The system according to claim 1, wherein the adjustment of the well is configured to be carried out electrically.

22. The system according to claim 21, wherein said adjustment is enabled by a remote control.

23. A system for adjusting an insertion depth of an insertable element associated with a portable therapeutic device, the system comprising:

a mounting unit securable to the skin of a patient and having a mounting base and a well defining a passageway through the mounting base, the well comprising a first part and a second part displaceable relative to the first part; and a cartridge unit including an insertable element for subcutaneous insertion through the well of the mounting unit, wherein the second part of the well and the cartridge unit are configured and arranged to define a space therebetween for receiving an adjustment tool in the space to adjust an insertion depth of the insertable element within the body of the patient.

* * * * *